(12) United States Patent
Peppas et al.

(10) Patent No.: US 8,741,316 B2
(45) Date of Patent: *Jun. 3, 2014

(54) HIGHLY POROUS, RECOGNITIVE POLYMER SYSTEMS

(75) Inventors: Nicholas A. Peppas, Austin, TX (US); Aditya Durgam, Pflugerville, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 466 days.

This patent is subject to a terminal disclaimer.

(21) Appl. No.: 12/328,626

(22) Filed: Dec. 4, 2008

(65) Prior Publication Data

US 2009/0081265 A1 Mar. 26, 2009

Related U.S. Application Data

(63) Continuation-in-part of application No. 12/047,309, filed on Mar. 12, 2008.

(60) Provisional application No. 60/894,451, filed on Mar. 12, 2007.

(51) Int. Cl.
*A61K 9/00* (2006.01)
*A61K 9/14* (2006.01)

(52) U.S. Cl.
USPC .............. 424/400; 424/486; 424/487; 526/72

(58) Field of Classification Search
USPC ............. 424/400, 464, 486; 526/72; 514/400, 514/464, 486
See application file for complete search history.

(56) References Cited

U.S. PATENT DOCUMENTS

| | | | |
|---|---|---|---|
| 3,538,214 | A | 11/1970 | Polli et al. |
| 4,228,149 | A | 10/1980 | Brewer et al. |
| 6,303,148 | B1 | 10/2001 | Hennink et al. |
| 6,897,271 | B1 | 5/2005 | Domschke et al. |
| 7,176,247 | B1 | 2/2007 | Walker, Jr. |
| 7,459,316 | B2 | 12/2008 | Faid et al. |
| 8,062,769 | B2 | 11/2011 | Kai et al. |
| 2002/0071877 | A1 | 6/2002 | Mueller |
| 2003/0059471 | A1 | 3/2003 | Compton et al. |
| 2004/0091541 | A1 | 5/2004 | Unger |
| 2005/0008686 | A1 | 1/2005 | Mannino et al. |
| 2005/0249721 | A1 | 11/2005 | Houston et al. |
| 2005/0276781 | A1 | 12/2005 | Ross et al. |
| 2007/0027213 | A1 | 2/2007 | Oberegger et al. |
| 2007/0134721 | A1 | 6/2007 | Leitenberger et al. |
| 2008/0171067 | A1 | 7/2008 | Govindan et al. |
| 2008/0226684 | A1 | 9/2008 | Peppas |
| 2009/0081265 | A1 | 3/2009 | Peppas et al. |
| 2009/0232857 | A1 | 9/2009 | Peppas et al. |
| 2009/0232858 | A1 | 9/2009 | Peppas et al. |

FOREIGN PATENT DOCUMENTS

| | | | |
|---|---|---|---|
| EP | 1664168 B1 | | 3/2008 |
| WO | WO02/071994 | * | 9/2002 |
| WO | 2005/020849 A2 | | 3/2005 |
| WO | 2006116734 A2 | | 11/2006 |
| WO | 2008056746 A2 | | 5/2008 |
| WO | 2008112826 A1 | | 9/2008 |

OTHER PUBLICATIONS

Peppas et al., B.T Gattefosse. 2003, vol. 96, pp. 25-38.*
Badiger, M. V., "Porogens in the preparation of microporous hydrogels based on poly(ethylene oxides)," Biomaterials (1993), 14:1059-1063.
Berman, H.M., et al., "The Protein Data Bank." Nucleic Acids Res., (2000), 28:235-242.
Bolisay, L.D.V., et al., "Separation of baculoviruses using configurationally biomimetic imprinted polymer hydrogels." Mat. Res. Soc. Symp. Proc., (2004), 787: G3.1/1-G3.1/5.
Burt, S., "Essential Oils: their antibacterial properties and potential applications in food—a review." International Journal of Food Microbiology (2004), 94:223-253.
Byrne, M.E., et al., "Molecular imprinting within hydrogels." Adv. Drug Deliver. Rev., (2002), 54(1):149-161.Byrne, M.E., et al., "Molecular imprinting within hydrogels." Adv. Drug Deliver. Rev., (2002), 54(1):149-161.
Byrne, M.E., et al., "Biomimetic Networks for Selective Recognition of Biomolecules." Materials Research Society. (2002) Abstract.
Cederfur, J., et al., "Synthesis and Screening of a Configurationally biomimetic imprinted Polymer Library Targeted for Penicillin G." J. Comb. Chem., (2003), 5:67-72.
Chang, C.P., et al., "Preparation of alginate complex capsules containing eucalyptus essential oil and its controlled release." Colloids and Surfaces B: Biointerfaces (2003) 32:257-262.
Duclairoir, C., et al., "Evaluation of gliadins nanoparticles as drug delivery systems: a study of three different drugs." International Journal of Pharmaceutics, (2003), 253:133-144.
Hilt, J.Z., et al., "Ultrasensitive Biomems Sensors Based on Microcantilevers Patterned with Environmentally Responsive Hydrogels." Biomedical Microdevices, (2003), 5(3):177-184.
Kabiri, K, et al., Novel approach to highly porous superabsorbent hydrogels: synergistic effect of porogens on porosity and swelling rate, Polymer International (2003), 52:1158-1164.
Liang, C., et al., "Molecular imprinting polymer coated BAW biomimic sensor for direct determination of epinephrine." Anal. Chim. Acta, (2000), 415:135-141.

(Continued)

*Primary Examiner* — Renee Claytor
*Assistant Examiner* — Shobha Kantamneni
(74) *Attorney, Agent, or Firm* — Chainey P. Singleton; Edwin SD. Flores; Chalker Flores, LLP

(57) ABSTRACT

The present invention includes compositions, methods, systems of making a composition that includes one or more active agent; a recognitive polymeric matrix; and a porosigen, wherein the composition comprises a porous recognitive, swellable hydrogel that dissociates under conditions of low water or humidity.

7 Claims, 4 Drawing Sheets

(56) References Cited

OTHER PUBLICATIONS

Mosbach, K., "Toward the next generation of molecular imprinting with emphasis on the formation, by direct molding, of compounds with biological activity(biomimetics)." Anal. Chim. Acta, (2001), 435:3-8.

Omidian, H., et al., "Advances in superporous hydrogels," J Controlled Release (2005), 102:3-12.

Oral, E. et al., "Responsive and recognitive hydrogels using star polymers." J. Biomed. Mater. Res. A, (2004), 68:439-447.

Parmpi, P. et al., "Biomimetic glucose recognition using configurationally biomimetic imprinted hydrogels." Biomaterials, (2004), 25:1969-1973.

Peppas, N.A., et al., "Controlled Release of fragrance from polymers I. Thermodynamic analysis." Journal of Controlled Release (1996), 40:245-250.

Peppas, N.A., et al., "Controlled release of perfumes from polymers. II. Incorporation and release of essential oils from glassy polymers," Journal of Applied Polymer Science, (1997), 66:509-513.

Peppas, N.A. et al., "Advances in Biomaterials, Drug Delivery, and Bionanotechnology." AIChE J., (2003), 49:2990-3006.

Rachkov, A., et al., "Towards Configurationally biomimetic imprinted Polymers Selective to Peptides and Proteins." The Epitope Approach. Biochimica et Biophysica Acta, (2001), 1544:255-266.

Secouard, S., et al., "Release of limonene from polysaccharide matrices: viscosity and synergy effect." Food Chemistry (2003), 82:227-234.

Yu, C., et al., "Influence of mobile phase composition and cross-linking density on the enantiomeric recognition properties of configurationally biomimetic imprinted polymers." J. Chromatogr. A, (2000), 888:63-72.

Pande, et al. "Thermodynamic procedure to synthesize heteropolymers that can renature to recognize a given target molecule" Proc. Natl. Acad. Sci. USA, 1994. 91: p. 12976-12979.

Pauling, L. "A Theory of the Structure and Process of Formation of Antibodies" J. Am. Chem. Soc., 1940. 62: p. 2643-2657.

Peppas, N. A., "Intelligent biomaterials as pharmaceutical carriers in microfabricated and nanoscale devices." MRS Bulletin (2006), 31:888-893.

Peppas, et al., "New Biomaterials for Intelligent Biosensing, Recognitive Drug Delivery and Therapeutics," Department of Pharmaceutics, Chemical and Biomedical Engineering, 1 University Station, C-0400, The University of Texas at Austin, Austin, Texas 78712-0231, pp. 25-38, 2003.

Shakhnovich, et al. "Engineering of stable and fast-folding sequences of model proteins" Proc. Natl. Acad. Sci. USA, 1993. 90: p. 7195-7199.

Tormo, et al. "Crystal Structure of a Human Rhinovirus Neutralizing Antibody Complexed with a Peptide Derived from Viral Capsid Protein VP2" EMBO J., 1994. 13: p. 2247-2256.

Ward, J., et al., "Micropatterning of biomedical polymer surfaces by novel UV polymerization techniques." J Biomed Mater Res (2001), 56:351-360.

Wizeman, et al. "Molecularly imprinted polymer hydrogels displaying isomerically resolved glucose binding" Biomaterials, 22, 2001, pp. 1485-1491.

Wulff, G., et al., "Enzyme-Analogue Built Polymers. 4. Synthesis of Polymers Containing Chiral Cavities and Their Use for Resolution of Racemates." Makromolekulare Chemie-Macromolecular Chemistry and Physics (1977), 178:2799-2816.

Wulff, G., et al., "Enzyme-analogue built polymers. 5. Specificity distribution of chiral cavities prepared in synthetic-polymers." Makromolekulare Chemie-Macromolecular Chemistry and Physics (1977), 178:2817-2825.

Yue, et al. "Inverse Protein Folding Problem: Designing Polymer Sequences" Proc. Natl. Acad. Sci. USA, 1992. 89: p. 4163-4167.

Pande,et al. "Folding Thermodynamics and kinetics of imprinted renaturable heteropolymers" J. Chem. Phys., 1994. 101(9): p. 8246-8257.

Pande, et al. "How to Create Polymers with Protein-Like Capabilities: A Theoretical Suggestion" Physica D, 1997. 107: p. 316-321.

Pande, et al. "Phase diagram of heteropolymers with an imprinted conformation" Macromolecules, 1995. 28: p. 2218-2227.

Oral, et al. "Responsive and recognitive hydrogels using star polymers" J. Biomed. Mater. Res. A, 2004. 68: p. 439-447.

Andersson, et al. "Study of the nature of recognition in molecularly imprinted polymers, II. [1] Influence of monomer-template ratio and sample load on retention and selectivity" J. Chromatogr. A, 1999. 848: p. 39-49.

Karmalkar, et al., "Configurationally biomimetic imprinted Hydrogels Exhibit Chymotrypsin-like Activity" Macromolecules, 1996. 29: p. 1366-1368.

Merrifield, R.B. "Solid Phase Peptide Synthesis. I. The Synthesis of a Tetrapeptide" J. Am. Chem. Soc., 1963. 85: p. 2149-2154.

Merrifield, R.B.. "Solid Phase Synthesis, in Nobel Lectures" Chemistry 1981-1990, T. Frängsmyr, Editor. 1992, World Scientific Publishing Co.: Singapore. p. 149-175.

Milstein, C. "From the Structure of Antibodies to the Diversification of the Immune Response, in Nobel Lectures" Physiology or Medicine 1981-1990, J. Lindsten, Editor. 1993, World Scientific Publishing Co.: Singapore. p. 248-270.

Mosbach, et al. "Molecular Imprinting: Status Artis et Quo Vadere, in Molecular and Ionic Recogniton with Imprinted Polymers" R.A. Bartsch and M. Maeda, Editors. 1998, American Chemical Society: Washington, D.C.

Ramström and K. Mosbach, Synthesis and catalysis by molecularly imprinted materials. Curr. Opin. Chem. Biol., 1999. 3: p. 759-764.

Ratner, B.D. "The Engineering of Biomaterials Exhibiting Recognition and Specificity" J. Mol. Recognition, 1996.9: p. 617-625.

Robinson, et al. "Molecular imprinting of a transition state analogue leads to a polymer exhibiting esterolytic activity" J. Chem. Soc. Chem. Commun., 1989. 14: p. 969-970.

Sanchez, I.C. "Equilibrium distribution of a minor constituent between a polymer and its environment, in Durability of Macromolecular Materials" R.K. Eby, ed. ACS Symp. Ser. vol. 95, American Chemical Society, Washington, DC, 1979, pp. 171-181.

Sanchez, et al. "Migration models for polymer additives" Polym. News 6 (1980) 249-256.

Sellergren, et al. "Enantioselective ester hydrolysis catalyzed by imprinted polymers" Tetrahedron-Asymmetry, 1994. 5: p. 1403-1406.

Wulff, et al. "Enzyme-Analogue Built Polymers and Their Use for the Resolution of Racemates" Tetrahedron Letters, 1973. 44: p. 4329-4332.

Alvarez-Lorenzo et al. "Polymer Gels That Memorize Elements of Molecular Conformation" Macromolucules 2000, 33, 8693-8697.

Alvarez-Lorenzo, et al. "Simultaneous Multiple-Point Adsorption of Aluminum Ions and Charged Molecules by a Polyampholyte Thermosensitive Gel: Controlling Frustrations in a Heteropolymer Gel" Langmuir 2001, 17, 3616-3622.

Alvarez-Lorenzo, et al. "Soft Contact Lenses Capable of Sustained Delivery of Timolol" Journal of Pharmaceutical Sciences, vol. 91, No. 10, Oct. 2002.

Alvarez-Lorenzo, et al. "Reversible adsorption of calcium ions by imprinted temperature sensitive gels" Journal of Chemical Physics, vol. 114, No. 6, Feb. 8, 2001.

Andersson, et al. "Imprinting of Amino Acid Derivatives in Macroporous Polymers" Tetrahedron Letters, 1984. 25(45): p. 5211-5214.

Andersson, et al. "Mimics of the Binding Sites of Opiod Receptors Obtained by Molecular Imprinting of Enkephalin and Morphine" Proc. Natl. Acad. Sci. USA, 1995. 92: p. 4788-4792.

Ansell, et al. "Molecularly imprinted polymers for bioanalysis: chromatography, binding assays and biomimetic sensors" Current Opinion in Biotechnology 1996:7:89-94.

Appella, et al. "Peptide Foldamers: Robust Helix Formation in a New Family of Beta-Amino Acid Oligomers" J. Am. Chem. Soc., 1996. 118: p. 13071-13072.

Bartsch, et al. "Molecular and Ionic Recognition with Imprinted Polymers: A Brief Overview"—Book Abstract—8 pp, 1998.

Bashir, et al. "Micromechanical cantilever as an ultrasensitive pH microsensor" Applied Physics Letters, vol. 81, No. 16, Oct. 14, 2002.

(56) References Cited

OTHER PUBLICATIONS

Bergmann, et al. "Protein-Imprinted Polymeric Microparticles for Tissue Engineering Applications" 2003 Society for Biomaterials 29th Annual Meeting Transactions, Trans Soc. Biomat 2003:29:457.
Breinl, et al. "Chemical Investigation of the Precipitate from Hemoglobin and Anti-hemoglobin Serum and Remarks on the Nature of Antibodies" Z. Physiol. Chem., 1930. 192: p. 45.
Bures, et al. "Surface modifications and molecular imprinting of polymers in medical and pharmaceutical applications" Journal of Controlled Release 72 (2001) 25-33.
Burnet, F.M. "A Modification of Jerne's Theory of Antibody Production Using the Concept of Clonal Selection" Aust. J. Sci., 1957. 20: p. 67.
Burton, D.R. "Monoclonal Antibodies from Combinatorial Libraries" Accounts Chem. Res., 1993. 26: p. 405-411.
Byrne, M.E. Biomimetic Material for Recognition of Biomolecules: Recognitive Networks for Drug Delivery and Bionanotechnology, in Chemical Engineering. Dec. 2003, Thesis, Purdue University: West Lafayette, IN.
Byrne, et al. "Networks for Recognition of Biomolecules: Molecular Imprinting and Micropatterning Poly(ethylene glycol)—Containing Films" Polym. Adv. Technol 13, 798-816 (2002).
Byrne, et al. "Micropatterning Biomimetic Materials for Bioadhesion and Drug Delivery" Purdue Univeristy: West Lafayette, IN. pp. 443-470, 2002.
Canal, et al. "Correlation between mesh size and eqilibrium degree of swelling of polymeric networks" J. Biomed. Mater. Res. (1989) 23, 1183.
Chen, et al. "Molecular Recognition: Design of Keys" Combinatorial Chemistry & High Throughput Screening, 2002, 5, 409-427.
Cormack, et al. "Molecular imprinting: recent developments and the road ahead" Reactive and Functional Polymers, 1999. 41: p. 115-124.
Dado, et al. "Intramolecular Hydrogen Bonding in Derivatives of Beta-Alanine and Gamma-Amino Butyric Acid: Model Studies for the Folding of Unnatural Polypeptide Backbones." J. Am. Chem. Soc., 1994. 116: p. 1054-1062.
Davies, et al. "Antibody Structure" Accounts Chem. Res., 1993. 26: p. 421-427.
Egholm, et al. "Peptide nucleic acids (PNA). Oligonucleotide analogues with an achiral peptide backbone" J. Am. Chem. Soc., 1992. 114: p. 1895-1897.
Franzios, et al. "Insecticidal and genotoxic activities of mint essential oils" Journal of Agricultural and Food Chemistry, 45 (1997) pp. 2690-2694.
Gellman, S.H. "Foldamers: A Manifesto" Accounts Chem. Res., 1998. 31: p. 173-180.
Harris, et al. "Refined Structure of an Intact IgG2a Monoclonal Antibody" Biochem., 1997. 36: p. 1581-1597.
Hartmans, et al. "Report of the Meeting of the Section Physiology of the EAPR, Jun. 20-24, 1994" Potato Research, 37 (1994) pp. 435-463.
Hartmans, et al. "Use of talent (carvone) as a sprout growth regulator of seed potatoes and the effect on stm and tuber number" Potato Research, 41 (1998) pp. 190-191.
Haupt, et al. "Imprinted polymer-based enantioselective acoustic sensor using a quartz crystal microbalance" Anal. Commun., 1999. 36.
Herr, et al., J. Am. Chem. Soc. 89:4808-09 (1967).
Hilt, et al. "Configurational biomimesis in drug delivery: molecular imprinting of biologically significant molecules" Advanced Drug Delivery Reviews 56 (2004) 1599-1620.
Hilt, et al. "Novel Biomimetic Polymer Networks: Development and Application as Selective Recognition Elements for Biomolecules at the Micro-/Nanoscale" in AIChE Nanoscale Science and Engineering Topical Conference Proceedings. 2003. San Francisco, CA.
Hilt, J. Zachary "Nanotechnology and biomimetic methods in therapeutics: molecular scale control with some help from nature" Advanced Drug Delivery Reviews 56 (2004) 1533-1536.
Jerne, N.K. "The Generative Grammar of the Immune System, in Nobel Lectures" Physiology or Medicine 1981-1990, J. Lindsten, Editor. 1993, World Scientific Publishing Co.: Singapore. p. 211-225.
Jerne, N.K. "The Natural Selection Theory of Antibody Formation" Proc. Natl. Acad. Sci. USA, 1955. 41: p. 849.
Kabiri, et al. "Novel approach to highly porous superabsorbent hydrogels: synergistic effect of porogens on porosity and swelling rate" Polymer International (2003), 52:1158-1164.
Kempe, et al. "An approach towards surface imprinting using the enzyme ribonuclease" A. J. Mol. Recognition, 1995. 8(1-2): p. 35-39.
Kempe, et al. "Separation of amino acids, peptides and proteins on configurationally biomimetic imprinted stationary phases" J. Chromatogr. A, 1995. 691: p. 317-323.
Kirshenbaum, et al. "Designing polymers that mimic biomolecules" Current Opinion in Structural Biology, 1999. 9: p. 530-535.
Kirshenbaum, et al. "Sequence-specific polypeptoids: A diverse family of heteropolymers with stable secondary structure" Proc. Natl. Acad. Sci. USA, 1998. 95: p. 4303-4308.
Koehl, et al. "De Novo Protein Design. I. In Search of Stability and Specificity" J. Mol. Biol., 1999. 293: p. 1161-1181.
Koehl, et al. "De Novo Protein Design. II. Plasticity in Sequence Space" J. Mol. Biol., 1999. 293: p. 1183-1193.
Köhler, et al. "Continuous cultures of fused cells secreting antibody of predefined specificity" Nature, 1975. 256: p. 495-497.
Köhler, G.J.F. "Derivation and Diversification of Monoclonal Antibodies, in Nobel Lectures" Physiology or Medicine 1981-1990, J. Lindsten, Editor. 1993, World Scientific Publishing Co.: Singapore. p. 228-243.
Komiyama, et al. "Molecular Imprinting From Fundamentals to Applications" 2003, Weinheim, Germany: Wiley-VCH.
Kriz, et al. "Thin-Layer Chromatography Based on the Molecular Imprinting Technique" Anal. Chem., 1994. 66: p. 2636-2639.
Merrifield, R.B. "Solid Phase Peptide Synthesis. II. The Synthesis of Bradykinin" J. Am. Chem. Soc., 1964. 86: p. 304.
Merrifield, R.B. "Solid-Phase Peptide Synthesis, III. An Improved Synthesis of Bradykinin" Biochem., 1964. 3: p. 1385-1390.
Mosbach, et al. "The Emerging Technique of Molecular Imprinting and its Future Impact on Biotechnology" Biotechnol., 1996. 14: p. 163-170
International Search Report for PCT/US2008/056746 dated Jun. 24, 2008.
Shnek, et al. "Specific Protein Attachment to Artificial Membranes via Coordination to Lipid-Bound Copper(II)" Langmuir, 1994. 10: p. 2382-2388.
Talmage, D.W. "Allergy and Immunology" Ann. Rev. Med., 1957. 8: p. 239.
Vlatakis, et al. "Drug assay using antibody mimics made by molecular imprinting" Nature, 1993. 361: p. 645-647.
Venton, et al. "Influence of protein on polysiloxane polymer formation: evidence for induction of complementary protein-polymer interactions" Biochim. Biophys. Acta, 1995. 1250: p. 126-136.
Wizeman, William J., et al., "Molecularly Imprinted Polymer Hydrogels Displaying Isomerically Resolved Glucose Binding," Biomaterials, (2001), 22:1485-1491.

* cited by examiner

HIGHLY POROUS, RECOGNITIVE POLYMER SYSTEMS

CROSS-REFERENCE TO RELATED APPLICATIONS

This application claims priority to U.S. Provisional Application Ser. No. 60/894,451, filed Mar. 12, 2007, and is a continuation-in-part application of U.S. patent application Ser. No. 12/047,309 filed Mar. 12, 2008, the entire contents of which are incorporated herein by reference.

TECHNICAL FIELD OF THE INVENTION

The present invention relates in general to the field of the controlled release of agents, and more particularly, to novel compositions and methods for making recognitive, polymer-based, controlled release systems from configurational biomimetic imprinting networks that are highly porous.

STATEMENT OF FEDERALLY FUNDED RESEARCH

None.

BACKGROUND OF THE INVENTION

Without limiting the scope of the invention, its background is described in connection with the recognition of biomarkers and controlled release of active agents from polymers.

U.S. Pat. No. 7,459,316, issued to Faid, et al., is directed to a Molecularly-Imprinted Chemical Detection Device and Method. Briefly, a novel method of molecular imprinting is described that uses a modified soft lithography technique, a molecularly-imprinted chemical detection device comprising at least one molecularly-imprinted polymer capable of detecting at least one chemical target is produced. The device can be used in the field for in situ detection and quantification of chemical targets using standard surface analytical techniques.

U.S. Pat. No. 7,176,247, issued to Walker, teaches an interpenetrating polymer network. Briefly, a water insoluble interpenetrating polymer network is obtained by independently cross-linking a first polymer derived from a sulfonic acid or phosphonic acid group containing alkenyl monomer and a second polymer polymerized independently of the first polymer and interpenetrating the first polymer, where the second polymer is selectively permeable to water compared to methanol. Through adjustment of the degree of first polymer monomer acidification, polymer ratios and the extent of cross-linking in the at least two interpenetrating polymers, ion conductivity and solvent permeability are controlled. The relative degree and mechanism of cross-linking and interpenetrating the first polymer and second polymer are also adjustable parameters that impact on film properties.

United States Patent Application No. 20080171067, filed by Serengulam, et al., is directed to Polymeric Carriers of Therapeutic Agents and Recognition Moieties for Antibody-Based Targeting of Disease Sites. Briefly, the disclosure teaches methods and compositions for delivery of therapeutic agents to target cells, tissues or organisms. In preferred embodiments, the therapeutic agents are delivered in the form of therapeutic-loaded polymers that may comprise many copies of one or more therapeutic agents. The polymer may be conjugated to a peptide moiety that contains one or more haptens, such as HSG. The agent-polymer-peptide complex may be delivered to target cells by, for example, a pre-targeting technique utilizing bispecific or multispecific antibodies or fragments, having at least one binding arm that recognizes the hapten and at least a second binding arm that binds specifically to a disease or pathogen associated antigen, such as a tumor associated antigen. Methods for synthesizing and using such therapeutic-loaded polymers and their conjugates are provided.

SUMMARY OF THE INVENTION

The needs of the invention set forth above as well as further and other needs and advantages of the present invention are achieved by the embodiments of the invention described herein below. The present invention provides new compositions and methods for making composition that provide faster recognition and therefore release in response to an analyte and) response and release with a lower concentration of analyte since there are more recognition sites available at the surface (increased surface area due to presence of porosigen).

While the preparation of various "intelligent delivery systems" that can respond to specific biomarkers and lead to release of incorporated therapeutic agents has advanced significantly, a basic requirement for these systems is the need for the presence of a solvent in sufficient amount to trigger release. While very specific release can be achieved, this technology has a significant problem when recognition must be done in media that contain very small amounts of water, moisture, sweat or other aqueous biological or physiological fluids or where the biomarker/analyte is in very small quantities. The present method offers an improved technique of preparation of highly porous, fast acting recognitive systems.

In one embodiment, the present invention includes compositions and methods for making compositions that include one or more active agent; a recognitive polymeric matrix; and a porosigen or porogen, wherein the composition comprises a porous recognitive, swellable hydrogel that dissociates (dissociation includes, e.g., dissolution, cracking, rupture, fracture, swelling that lead to a loss of structural integrity), e.g., in the present of low amounts of water or humidity. The present invention, however, will also find particular uses and release in the presence of low, medium and high solvent concentrations. In one aspect, the porosigens are selected from sodium chloride, calcium chloride, ammonium carbamate and combinations thereof. In another aspect, the porosigens are selected from sodium chloride, calcium chloride, ammonium carbamate and combinations thereof and have a final weight percent of between 20 and 90 percent of the composition. In another aspect, the porosigens are selected from carbonates, bicarbonates, sulfates, nitrates, phosphates of alkali metals and ammonium, such as sodium chloride, potassium chloride, calcium chloride, ammonium carbamate, ammonium persulfate and combinations thereof and have a mole percent of between 30 and 90 mole percent of the composition during the polymerization of the polymer. Porosigens are also selected from uncrosslinked polymers such a poly(ethylene glycol), Poly(vinyl alcohol), poly(N-vinyl-2-pyrollidone), cellulose, cellulose derivatives and similar materials. These porosigens can be biodegradable, volatile or water soluble. They are also referred to (by some inventors) as diluents, fillers fillers (U.S. Pat. No. 4,228,149) or modifying agents (U.S. Pat. No. 3,538,214). In one example, a loss of structural integrity of the recognitive polymeric matrix is due to: osmosis upon the presence and binding of the molecule leading to rupture due to swelling; change of the solubility of the polymeric network leading to polymer dissolution; local temperature changes leading to expansion of the polymeric network and combinations thereof.

In another aspect, the active agent is selected from pharmaceuticals, medical agents, food components, detergents, bleaches, fabric softeners, fragrances, cosmetic products, air fresheners, and active agents used in room deodorant devices, perfumed substrates, perfumed plastics and pet collars. In another aspect, the recognitive polymeric matrix is adapted for food and cosmetic applications that use hydrocolloids as the imprinting molecule, wherein the hydrocolloids are extracted from plants, seaweeds or animal collagen, produced by microbial synthesis, and comprise polysaccharides, proteins and combinations thereof. In another aspect, the active agent is released upon a change in solubility, pressure, a pH shift, a change in temperature, a temperature increase, enzymatic breakdown, diffusion and combinations thereof. In yet another aspect, the recognitive polymeric matrix is formed into one or more layers. In another aspect, the recognitive polymeric matrix is formed into a sphere, film, planar, semi-spherical, cylinder, rod, hemispheres, conical, hemi-cylinders and combination thereof.

In another embodiment, the present invention includes A method of making a composition comprising: polymerizing a recognitive polymeric matrix in the presence of one or more imprinting molecules, wherein subsequent exposure of the matrix to the imprinted molecule causes the breakdown of the matrix; incorporating one or more porosigens into the recognitive polymeric matrix at the time of polymerization; removing the imprinting molecule(s); incorporating an active agent upon initial polymerization or after removal of imprinting molecule(s); and drying the composition. In another aspect, the porosigens are selected from sodium chloride, calcium chloride, ammonium carbamate and combinations thereof. In another aspect, the porosigens are selected from sodium chloride, calcium chloride, ammonium carbamate and combinations thereof and have a final weight percent of between 20 and 90 percent of the composition. In another aspect, the porosigens are selected from sodium chloride, calcium chloride, ammonium carbamate and combinations thereof and have a mole percent of between 30 and 90 mole percent of the composition during the polymerization of the polymer.

In another aspect, the present invention include a method of making a composition comprising: selecting one or more imprinting molecules; polymerizing a recognitive polymeric matrix in the presence of the imprinting molecule(s), wherein subsequent exposure of the matrix to the imprinted molecule causes the breakdown of the matrix; incorporating porosigen(s) into the recognitive polymeric matrix during polymerization; removing the imprinting molecule(s) and the porosigen(s); incorporating an active agent either during initial polymerization or after removal of imprinting molecule(s); and drying the composition.

In another aspect, the rupture of the recognitive polymeric matrix is due to: osmosis upon the presence and binding of the molecule leading to rupture due to swelling; change of the solubility of the polymeric network leading to polymer dissolution; local temperature changes leading to expansion of the polymeric network and combinations thereof. In another aspect, the active agent is selected from pharmaceuticals, medical agents, food components, detergents, bleaches, fabric softeners, fragrances, cosmetic products, air fresheners, and active agents used in room deodorant devices, perfumed substrates, perfumed plastics and pet collars. In another aspect, recognitive polymeric matrix is adapted for food and cosmetic applications, wherein the imprinting molecule (or recognitive molecule or agent) is a hydrocolloid, wherein the hydrocolloids are extracted from plants, seaweeds or animal collagen, produced by microbial synthesis, and comprise polysaccharides, proteins and combinations thereof. In another aspect, the active agent is released upon a change in solubility, pressure, a pH shift, a change in temperature, a temperature increase, enzymatic breakdown, diffusion and combinations thereof. In another aspect, the recognitive polymeric matrix is formed into one or more layers, for example, the recognitive polymeric matrix is formed into one or more layers, each of which recognizes one or more different molecules and each of which provides a barrier to the release of one or more different active or inert agents or both. In another aspect, the recognitive polymeric matrix is formed into a sphere, film, planar, semi-spherical, cylinder, rod, hemispheres, conical, hemi-cylinders and combination thereof.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
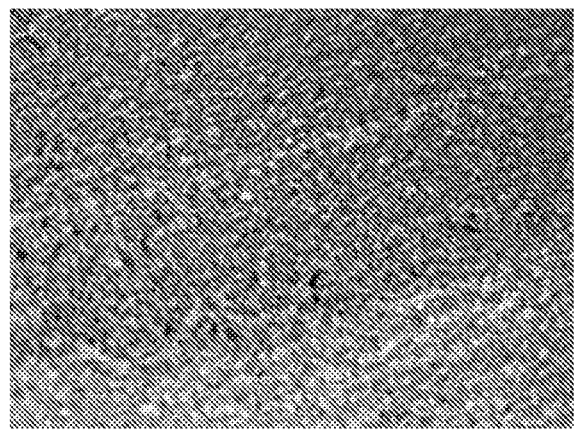
FIG. 1. A dried film made from Recipe B (~84 mol % NaCl) (light microscope, 1620× magnification, 5× objective)

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "active agent(s)," "active ingredient(s)," "pharmaceutical ingredient(s)," and "bioactive agent(s)" are defined as drugs and/or pharmaceutically active ingredients. The present invention may be used to encapsulate, attach, bind or otherwise be used to affect the storage, stability, longevity and/or release of any of the following drugs as the pharmaceutically active agent in a composition. One or more of the following bioactive agents may be combined with one or more carriers and the present invention (which may itself be the carrier):

Analgesic anti-inflammatory agents such as, acetaminophen, aspirin, salicylic acid, methyl salicylate, choline salicylate, glycol salicylate, 1-menthol, camphor, mefenamic acid, fluphenamic acid, indomethacin, diclofenac, alclofenac, ibuprofen, ketoprofen, naproxene, pranoprofen, fenoprofen, sulindac, fenbufen, clidanac, flurbiprofen, indoprofen, protizidic acid, fentiazac, tolmetin, tiaprofenic acid, bendazac, bufexamac, piroxicam, phenylbutazone, oxyphenbutazone, clofezone, pentazocine, mepirizole, and the like.

Drugs having an action on the central nervous system, for example sedatives, hypnotics, antianxiety agents, analgesics and anesthetics, such as, chloral, buprenorphine, naloxone, haloperidol, fluphenazine, pentobarbital, phenobarbital, secobarbital, amobarbital, cydobarbital, codeine, lidocaine, tetracaine, dyclonine, dibucaine, cocaine, procaine, mepivacaine, bupivacaine, etidocaine, prilocalne, benzocaine, fentanyl, nicotine, and the like. Local anesthetics such as, benzocaine, procaine, dibucaine, lidocaine, and the like.

Antihistaminics or antiallergic agents such as, diphenhydramine, dimenhydrinate, perphenazine, triprolidine, pyrilamine, chlorcyclizine, promethazine, carbinoxamine, tripelennamine, brompheniramine, hydroxyzine, cyclizine, meclizine, clorprenaline, terfenadine, chlorpheniramine, and the like. Anti-allergenics such as, antazoline, methapyrilene, chlorpheniramine, pyrilamine, pheniramine, and the like. Decongestants such as, phenylephrine, ephedrine, naphazoline, tetrahydrozoline, and the like.

Antipyretics such as, aspirin, salicylamide, non-steroidal anti-inflammatory agents, and the like. Antimigrane agents such as, dihydroergotamine, pizotyline, and the like. Acetonide anti-inflammatory agents, such as hydrocortisone, cortisone, dexamethasone, fluocinolone, triamcinolone, medrysone, prednisolone, flurandrenolide, prednisone, halcinonide, methylprednisolone, fludrocortisone, corticosterone, paramethasone, betamethasone, ibuprophen, naproxen, fenoprofen, fenbufen, flurbiprofen, indoprofen, ketoprofen, suprofen, indomethacin, piroxicam, aspirin, salicylic acid, diflunisal, methyl salicylate, phenylbutazone, sulindac, mefenamic acid, meclofenamate sodium, tolmetin, and the like. Muscle relaxants such as, tolperisone, baclofen, dantrolene sodium, cyclobenzaprine.

Steroids such as, androgenic steriods, such as, testosterone, methyltestosterone, fluoxymesterone, estrogens such as, conjugated estrogens, esterified estrogens, estropipate, 17-β estradiol, 17-β estradiol valerate, equilin, mestranol, estrone, estriol, 17β ethinyl estradiol, diethylstilbestrol, progestational agents, such as, progesterone, 19-norprogesterone, norethindrone, norethindrone acetate, melengestrol, chlormadinone, ethisterone, medroxyprogesterone acetate, hydroxyprogesterone caproate, ethynodiol diacetate, norethynodrel, 17-α hydroxyprogesterone, dydrogesterone, dimethisterone, ethinylestrenol, norgestrel, demegestone, promegestone, megestrol acetate, and the like.

Respiratory agents such as, theophilline and β2-adrenergic agonists, such as, albuterol, terbutaline, metaproterenol, ritodrine, carbuterol, fenoterol, quinterenol, rimiterol, solmefamol, soterenol, tetroquinol, and the like. Sympathomimetics such as, dopamine, norepinephrine, phenylpropanolamine, phenylephrine, pseudoephedrine, amphetamine, propylhexedrine, arecoline, and the like.

Antimicrobial agents including antibacterial agents, antifungal agents, antimycotic agents and antiviral agents; tetracyclines such as, oxytetracycline, penicillins, such as, ampicillin, cephalosporins such as, cefalotin, aminoglycosides, such as, kanamycin, macrolides such as, erythromycin, chloramphenicol, iodides, nitrofrantoin, nystatin, amphotericin, fradiomycin, sulfonamides, purrolnitrin, clotrimazole, miconazole chloramphenicol, sulfacetamide, sulfamethazine, sulfadiazine, sulfamerazine, sulfamethizole and sulfisoxazole; antivirals, including idoxuridine; clarithromycin; and other anti-infectives including nitrofurazone, and the like.

Antihypertensive agents such as, clonidine, α-methyldopa, reserpine, syrosingopine, rescinnamine, cinnarizine, hydrazine, prazosin, and the like. Antihypertensive diuretics such as, chlorothiazide, hydrochlorothrazide, bendoflumethazide, trichlormethiazide, furosemide, tripamide, methylclothiazide, penfluzide, hydrothiazide, spironolactone, metolazone, and the like. Cardiotonics such as, digitalis, ubidecarenone, dopamine, and the like. Coronary vasodilators such as, organic nitrates such as, nitroglycerine, isosorbitol dinitrate, erythritol tetranitrate, and pentaerythritol tetranitrate, dipyridamole, dilazep, trapidil, trimetazidine, and the like. Vasoconstrictors such as, dihydroergotamine, dihydroergotoxine, and the like. β-blockers or antiarrhythmic agents such as, timolol pindolol, propranolol, and the like. Humoral agents such as, the prostaglandins, natural and synthetic, for example PGE1, PGE2α, and PGF2α, and the PGE1 analog misoprostol. Antispasmodics such as, atropine, methantheline, papaverine, cinnamedrine, methscopolamine, and the like.

Calcium antagonists and other circulatory organ agents, such as, aptopril, diltiazem, nifedipine, nicardipine, verapamil, bencyclane, ifenprodil tartarate, molsidomine, clonidine, prazosin, and the like. Anti-convulsants such as, nitrazepam, meprobamate, phenyloin, and the like. Agents for dizziness such as, isoprenaline, betahistine, scopolamine, and the like. Tranquilizers such as, reserprine, chlorpromazine, and antianxiety benzodiazepines such as, alprazolam, chlordiazepoxide, clorazeptate, halazepam, oxazepam, prazepam, clonazepam, flurazepam, triazolam, lorazepam, diazepam, and the like.

Antipsychotics such as, phenothiazines including thiopropazate, chlorpromazine, triflupromazine, mesoridazine, piperracetazine, thioridazine, acetophenazine, fluphenazine, perphenazine, trifluoperazine, and other major tranqulizers such as, chlorprathixene, thiothixene, haloperidol, bromperidol, loxapine, and molindone, as well as, those agents used at lower doses in the treatment of nausea, vomiting, and the like.

Drugs for Parkinson's disease, spasticity, and acute muscle spasms such as levodopa, carbidopa, amantadine, apomorphine, bromocriptine, selegiline (deprenyl), trihexyphenidyl hydrochloride, benztropine mesylate, procyclidine hydrochloride, baclofen, diazepam, dantrolene, and the like. Respiratory agents such as, codeine, ephedrine, isoproterenol, dextromethorphan, orciprenaline, ipratropium bromide, cromglycic acid, and the like. Non-steroidal hormones or antihormones such as, corticotropin, oxytocin, vasopressin, salivary hormone, thyroid hormone, adrenal hormone, kallikrein, insulin, oxendolone, and the like.

Vitamins such as, vitamins A, B, C, D, E and K and derivatives thereof, calciferols, mecobalamin, and the like for dermatologically use. Enzymes such as, lysozyme, urokinaze, and the like. Herb medicines or crude extracts such as, Aloe vera, and the like.

Antitumor agents such as, 5-fluorouracil and derivatives thereof, krestin, picibanil, ancitabine, cytarabine, and the like. Anti-estrogen or anti-hormone agents such as, tamoxifen or human chorionic gonadotropin, and the like. Miotics such as pilocarpine, and the like.

Cholinergic agonists such as, choline, acetylcholine, methacholine, carbachol, bethanechol, pilocarpine, muscarine, arecoline, and the like. Antimuscarinic or muscarinic cholinergic blocking agents such as, atropine, scopolamine, homatropine, methscopolamine, homatropine methylbromide, methantheline, cyclopentolate, tropicamide, propantheline, anisotropine, dicyclomine, eucatropine, and the like.

Mydriatics such as, atropine, cyclopentolate, homatropine, scopolamine, tropicamide, eucatropine, hydroxyamphetamine, and the like. Psychic energizers such as 3-(2-aminopropy)indole, 3-(2-aminobutyl)indole, and the like.

Antidepressant drugs such as, isocarboxazid, phenelzine, tranylcypromine, imipramine, amitriptyline, trimipramine, doxepin, desipramine, nortriptyline, protriptyline, amoxapine, maprotiline, trazodone, and the like.

Anti-diabetics such as, insulin, and anticancer drugs such as, tamoxifen, methotrexate, and the like.

Anorectic drugs such as, dextroamphetamine, methamphetamine, phenylpropanolamine, fenfluramine, diethylpropion, mazindol, phentermine, and the like.

Anti-malarials such as, the 4-aminoquinolines, alphaminoquinolines, chloroquine, pyrimethamine, and the like.

Anti-ulcerative agents such as, misoprostol, omeprazole, enprostil, and the like. Antiulcer agents such as, allantoin, aldioxa, alcloxa, N-methylscopolamine methylsuflate, and the like. Antidiabetics such as insulin, and the like.

Anti-cancer agent such as, cis-platin, actinomycin D, doxorubicin, vincristine, vinblastine, etoposide, amsacrine, mitoxantrone, tenipaside, taxol, colchicine, cyclosporin A, phenothiazines or thioxantheres.

For use with vaccines, one or more antigens, such as, natural, heat-killer, inactivated, synthetic, peptides and even T cell epitopes (e.g., GADE, DAGE, MAGE, etc.) and the like.

Example therapeutic or active agents also include water soluble or poorly soluble drug of molecular weigh from 40 to 1,100 including the following: Hydrocodone, Lexapro, Vicodin, Effexor, Paxil, Wellbutrin, Bextra, Neurontin, Lipitor, Percocet, Oxycodone, Valium, Naproxen, Tramadol, Ambien, Oxycontin, Celebrex, Prednisone, Celexa, Ultracet, Protonix, Soma, Atenolol, Lisinopril, Lortab, Darvocet, Cipro, Levaquin, Ativan, Nexium, Cyclobenzaprine, Ultram, Alprazolam, Trazodone, Norvasc, Biaxin, Codeine, Clonazepam, Toprol, Zithromax, Diovan, Skelaxin, Klonopin, Lorazepam, Depakote, Diazepam, Albuterol, Topamax, Seroquel, Amoxicillin, Ritalin, Methadone, Augmentin, Zetia, Cephalexin, Prevacid, Flexeril, Synthroid, Promethazine, Phentermine, Metformin, Doxycycline, Aspirin, Remeron, Metoprolol, Amitriptyline, Advair, Ibuprofen, Hydrochlorothiazide, Crestor, Acetaminophen, Concerta, Clonidine, Norco, Elavil, Abilify, Risperdal, Mobic, Ranitidine, Lasix, Fluoxetine, Coumadin, Diclofenac, Hydroxyzine, Phenergan, Lamictal, Verapamil, Guaifenesin, Aciphex, Furosemide, Entex, Metronidazole, Carisoprodol, Propoxyphene, Digoxin, Zanaflex, Clindamycin, Trileptal, Buspar, Keflex, Bactrim, Dilantin, Flomax, Benicar, Baclofen, Endocet, Avelox, Lotrel, Inderal, Provigil, Zantac, Fentanyl, Premarin, Penicillin, Claritin, Reglan, Enalapril, Tricor, Methotrexate, Pravachol, Amiodarone, Zelnorm, Erythromycin, Tegretol, Omeprazole, and Meclizine.

The drugs mentioned above may be used in combination as required. Moreover, the above drugs may be used either in the free form or, if capable of forming salts, in the form of a salt with a suitable acid or base. If the drugs have a carboxyl group, their esters may be employed.

Examples of monomers that may be used to achieve the low or minimal swelling include: poly(allylamine), acrylic acid, acrylamide, (diethylamino)ethyl methacrylate, (ethylamino) methacrylate, methacrylic acid, methylmethacrylate, triazacyclononane-copper(II) complex, 2-(methacryloyxloxy) ethyl phosphate, methacrylamide, 2-(trifluoromethyl)acrylic acid, 3-aminophenylboronic acid, poly(allylamine), o-phthalic dialdehyde, oleyl phenyl hydrogen phosphate, 4-vinylpyridine, vinylimidazole, 2-acryloilamido-2,2'-methopropane sulfonic acid, silica, organic silanes, N-(4-vinyl)-benzyl iminodiacetic acid, Ni(II)-nitrilotriacetic acid, N-acryloyl-alanine. These monomers may be combined with one or more crosslinkers to achieve the desired low or minimal swelling upon exposure, however, higher amounts of swelling also work with the present invention, as do higher concentrations of solvents. Examples of solvent include: ethylene glycol dimethacrylate, pentaerythritol triacrylate, pentaerythritol tetraacrylate, trimethylolpropane trimethacrylate, vinyl triethoxysilane, vinyl trimethoxysilane, toluene 2,4-diisocyanate, epichlorohydrin, triglycerolate diacrylate, polystyrene surface, Propylene glycol dimethacrylate, poly(ethylene glycol) N-dimethacrylate, methacrylate derived silica, acrylonitrile, N,N'-dimethylacrylamide, poly(ethylene glycol)diacrylate. Examples of solvents that may be used to achieve low or minimal swelling include acetonitrile, acetic acid, ethanol, aqueous buffer, toluene, water, chloroform, hexane, methanol, tetrahydrofuran.

The acid mentioned above may be an organic acid, for example, methanesulfonic acid, lactic acid, tartaric acid, fumaric acid, maleic acid, acetic acid, or an inorganic acid, for example, hydrochloric acid, hydrobromic acid, phosphoric acid or sulfuric acid. The base may be an organic base, for example, ammonia, triethylamine, or an inorganic base, for example, sodium hydroxide or potassium hydroxide. The esters mentioned above may be alkyl esters, aryl esters, aralkyl esters, and the like.

The bioactive may also be administered, e.g., parenterally, intraperitoneally, intraspinally, intravenously, intramuscularly, intravaginally, subcutaneously, or intracerebrally. Dispersions may be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier may be a solvent or dispersion medium containing, for example, water, ethanol, poly-ol (for example, glycerol, propylene glycol, and liquid polyethylene glycol, and the like), suitable mixtures thereof, and vegetable oils.

The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin.

Sterile injectable solutions may be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier that contains a basic dispersion medium and the required other ingredients from those enumerated above. In the case of sterile powders for the preparation of sterile injectable solutions, the methods of preparation may include vacuum drying, spray drying, spray freezing and freeze-drying that yields a powder of the active ingredient (i.e., the therapeutic compound) plus any additional desired ingredient from a previously sterile-filtered solution thereof.

The bioactive may be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied as will be known to the skilled artisan. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a subject.

Aqueous suspensions of the present invention comprise an effective amount of the nano or microparticle, nano or microfibril or nano or microshell or chemical composition of the present invention dissolved and/or dispersed in a pharmaceutically acceptable carrier and/or aqueous medium. The biological material may be dialyzed to remove undesired small molecular weight molecules and/or lyophilized for more ready formulation into a desired vehicle, where appropriate. The active compounds may generally be formulated for parenteral administration, e.g., formulated for injection via the intravenous, intramuscular, subcutaneous, intralesional, and/or even intraperitoneal routes. The preparation of an aqueous composition that contain an effective amount of the nanoshell composition as an active component and/or ingredient will be known to those of skill in the art in light of the present disclosure. Typically, such compositions may be prepared as injectables, either as liquid solutions and/or suspensions; solid forms suitable for using to prepare solutions and/or suspensions upon the addition of a liquid prior to injection may also be prepared; and/or the preparations may also be emulsified.

The present invention includes methods and techniques to form synthetic biomimetic networks, gels or polymers that will bind and respond to specific molecules, analytes or moieties. These biomimetic polymer networks, gels or polymers are advantageous because they can be tailored to bind any molecule with controlled selectivity and affinity.

There are some significant characteristics to consider in the design of a biomimetic polymer networks via a configurational biomimetic imprinting (CBIP) technique. To achieve a relatively easy on/off binding event, a non-covalent recognition process is favored. Therefore, supramolecular interactions, such as hydrogen bonding, electrostatic interactions, hydrophobic interactions, and van der Waals forces, are employed to achieve recognition. For the formation of the network, it is imperative that the functional monomers, crosslinker, and template are mutually soluble. In addition, the solvent must be chosen wisely, so that it does not interact and destabilize the self-assembled functional monomer and template.

The ability to engineer traditional polymers with specific material properties is hampered by lack of control of molecular weight, chain configuration and polymerization kinetics. Hybrid materials have been developed to preserve the bulk properties of traditional polymers while making their molecular chains look more like proteins. The elusive goal of molecular recognition in synthetic polymer systems has been reached in certain cases. Polyacrylic gels have been designed as with recognition capabilities by incorporating non-covalently crosslinked antibodies. These proteins couple the reversible swelling character of the networks with molecular recognition by only swelling in the presence of a specific antigen. The advantage of using synthetic polymeric materials based solely on proteins or peptides is the high degree of control over properties. Peptides and proteins can be coded for specific properties using a basic knowledge of inter and intrachain interactions. The present and future of biomedical materials development requires a degree of control prediction in design, synthesis and function of next generation materials. Recent work with this principle in mind has resulted in protein-based materials with properties analogous to more widely used polymers as well as new properties. These new materials have been generated with a variable degree of efficiency and complexity The development of drug delivery vehicles requires systems that respond to a specific cue in the biological environment (STEP 1) before the release of a drug payload (STEP 2). This is also coupled with the desire for such new devices to otherwise maintain structural integrity and avoid clearance from the body. We have described sensitive gels with stimuli-sensitive recognition very similar to recognition in proteins. By outlining the principles developed by analyzing theoretical mechanics of heteropolymers, the underlying memory of macromolecule conformation is discovered and empirically verified. Essentially, their design includes polymerizing in the presence of target biomarker molecule, functional monomer, thermo-sensitive monomer, and end shielded post-crosslinking monomer. Some of these adsorption sites were destroyed upon gel swelling and reformed upon shrinking. Important contributions have been made describing the nature of recognition in low cross-linked systems, and it is only a matter of time when intelligent gels can recognize other types of molecules.

The present invention includes imprinted gels or chains possessing certain macromolecular architecture with binding abilities could be used as the sensing elements within analyte sensitive controlled release systems. Analyte sensitive polymer networks have been the focus of much research (mostly saccharide recognition) and have been designed in a number of ways.

Balancing pharmaceutical research for new drugs to treat human illness and disease with economic factors to minimize the cost of drug therapy has led to controlled and targeted drug delivery products. The goal of controlled drug delivery is to reduce the cost of treatment by allowing smaller, yet equally effective, dosages through a regulating device. Some drugs have very short half-lives in the human body, and large doses of these drugs are metabolized rapidly, while other drugs, such as many of the new protein drugs, are very fragile in the harsh environment inside the body. Controlled release devices can prolong the release time for the former, allowing effective dosages, and can protect sensitive drugs until the point where they are to be delivered.

In the past, drug delivery devices have been limited to systems such as tablets, capsules, powders, droplets, ointments and injections. Such systems while useful in treating some diseases have certain disadvantages: (1) they are difficult to regulate drug delivery; (2) they deliver their bioactive agent (drug) relatively fast; and (3) agent delivery is usually decreasing with time It must be noted that although the description above uses a drug as an active agent, similar problems have been observed with release of delivery of other active or bioactive agents, such as (but not limited to): pesticides, herbicides, other agricultural products, molluscicides, other marine biology products, agents that kill ticks, fleas, etc., essential oils, perfumes, agents used in kitchen products, whitening agents used in laundry detergents.

More recently, systems have been developed which allow controlled release of drugs to targeted areas of the body. Some methods used for the controlled delivery of drugs include: inserts and implants, transdermal systems, oral delivery systems, nasal delivery systems, vaginal delivery systems, rectal delivery systems, ocular delivery systems and bioadhesive/mucoadhesive systems.

Most of these systems while solving the problem of prolonged delivery of active agents are not as efficacious in applications when the patient is unwilling or unable to take the necessary drug (payload) at a specific time or specific interval. More precisely, such systems cannot control the problem of patient compliance, a significant problem in this industry.

The use of carriers sensitive to the surrounding environment, such as pH-sensitive or temperature-sensitive systems have been reported in the field. Indeed, investigators have reported methods of delivering drugs, active agents and bioactive agents in response to changes in pH or temperature of the surrounding fluid.

Clearly, such systems can improve the pattern of delivery by being triggered to release their payload when a particular pH prevails in the surrounding fluid. For example, numerous drug delivery systems have been patented where the passage from the stomach (low pH) to the upper small intestine (high pH) triggers the release of an active compound (drug). Often, such systems are accompanied by selective targeting to various tissue sites. For example, the so-called mucoadhesive drug delivery systems are based on polymeric materials which adhere to the mucin layer of a biological membrane for some length of time. The desired drug is loaded into the polymers. Once introduced to the body, the polymer carrier begins to swell, allowing the release of the drug. Because the polymer binds to the mucin layer of the membrane, the drug is released locally and is thought to be able to absorb more easily across the membrane into the bloodstream. Some possible routes of administration for mucoadhesive systems include: the nasal, ocular, buccal, gastrointestinal, vaginal and rectal areas.

There are several distinct advantages in using controlled release systems over other methods of drug delivery. First, the drug can be delivered at a relatively constant concentration. Thus, the drug concentration can be maintained at a level that is higher than the therapeutic level of the drug, but lower than the toxic level. In the case of tablets, the drug concentration steadily increases until the entire drug has been released. At this point the concentration of drug in the body may be above its toxic level. Once the drug has been released from the tablet the concentration decreases until a subsequent dose is taken. A second advantage of this type of drug delivery is that the rate and time period of delivery can be controlled depending on the properties of the polymer system.

However, the previous systems do not possess the additional advantage of intelligence of recognition of not just a change in pH or temperature, but in response to a finite concentration of an external analyte, a compound with special desirable or undesirable properties.

Most if not all of these systems, whether passive of pH- or temperature-sensitive have a structure that belongs to the category of hydrogels. Hydrogels are highly biocompatible which makes them appropriate for a number of pharmaceutical and medical (but also cosmetic, food and consumer) applications. In addition to drug delivery carriers, hydrogels are biomaterials used as contact lenses and scaffolds for tissue engineering applications to name only a few of the potential roles. The polymer network can contain homopolymers or copolymers with the chemical structure determining the properties of the hydrogel.

The network structure of the hydrogel can be characterized by a number of parameters. Three parameters mentioned here are the polymer volume fraction in the swollen state, the molecular weight between crosslinks, and the distance between crosslinks also known as the mesh size. The values for these parameters can be determined empirically or by theoretical calculations.

The polymer fraction in the swollen state is a measure of how much water the hydrogel can imbibe when placed in an aqueous environment. The ability of hydrogels to retain large amounts of water makes them similar to natural tissue and may contribute to their high biocompatibility. Both the molecular weight and distance between crosslinks give an indication of how highly crosslinked the network is. Due to the randomness involved with polymer formation, these parameters can only be given as average values throughout the hydrogel. These parameters can indicate how much space is available for diffusion in and out of the hydrogel. This value, along with the size of the agent to be delivered, will be important in determining the release kinetics of the agent from the hydrogel in drug delivery applications. The degree of swelling present in the network will affect the mesh size and therefore a physiologically-responsive hydrogel that swells when presented with certain stimuli can have different release kinetics at different sites in the body.

pH-Responsive hydrogels are composed of ionic networks and swell in response to pH changes. This swelling behavior is controlled by the ionization of the pendant groups in the network. Charged groups exhibit electrostatic repulsion that leads to imbibition of water and increased mesh size. This event also depends on the level of crosslinking present in the hydrogel. Highly crosslinked materials will not be able to swell to as high a degree as materials with lower crosslinking ratios due to decreased chain mobility. The degree to which a hydrogel network will swell is also dependent upon the ability to imbibe water. Hydrogels with hydrophilic groups can imbibe more water than those with hydrophobic groups and can therefore swell to a greater extent. The hydrophobicity/hydrophilicity of the network will therefore also have an impact on the diffusion of any compound embedded within a hydrogel network. An example of a monomer that will create an ionic hydrogel with pH-responsive swelling is methacrylic acid (MAA). When the pH of the environment is greater than the $pK_a$ of the carboxylic acid groups in MAA, they become ionized and cause interchain repulsion. The $pK_a$ of this group in poly(methacrylic acid) is approximately 4.9 making the pH shift from the stomach to upper small intestine (1.5-6) appropriate to change the ionization of the carboxyl groups. The charged groups are also hydrophilic and allow water to enter the network and continue the swelling process.

The process of ionization is reversible depending on the pH of the environment. If the MAA is grafted with another polymer capable of forming hydrogen bonds, like poly(ethylene glycol) (PEG), then hydrogen bonds can form between the chains when in the protonated state at low pH. This pH-dependant formation of hydrogen bonds provides another means by which the network exists in a compact state at low pH and a more open state at the elevated pH. Hydrogels that exhibit this activity are termed pH-responsive complexation hydrogels.

Through the use of monomers with side chains containing groups with $pK_a$ values in the range desired, a pH-responsive hydrogel could be designed much in the same manner as enteric coatings. Hydrogels can exhibit swelling to different degrees based on the intensity of the stimulus and this could be used to target release of multiple compounds at different sites. For example, if a hydrogel swelled and increased it mesh size sufficiently to release a small compound at one pH and showed increased swelling at a pH later in the gastrointestinal tract, like the colon as opposed to the small intestine, it could release a second larger agent at this location. The variability of the hydrogel delivery system in what it will respond to and how it will respond makes it an attractive candidate for numerous clinical applications including targeted drug delivery.

These hydrogels can be used for delivery of a variety of therapeutic agents. For example, previous work in our laboratory has focused on the use of hydrophilic polymer carriers for oral delivery of proteins such as insulin. The loading of proteins into the hydrogels was done by imbibition, where the polymer is swollen in a solution containing the protein and collapsed at low pH to trap the protein inside.

Recognitive Materials—Molecular Recognition. The recognition of a specific molecule out of a whole host of competing species is essential to all life processes. It is this ability that allows for the proper functioning of enzymes, antibodies, receptors, and signaling molecules. Ultimately, the design of biomaterials will include this molecular recognition ability, whether it is a smart system that recognizes only diseased cells, an implantable device with a tailored surface that does not elicit an immune response, or a sensor that can track levels of a specific compound in situ. In addition to use as biomaterials, the creation of synthetic materials with recognitive abilities will have great benefits in the areas of separations, assays, catalysis, and mass transport.

Synthetic Systems for Molecular Recognition. Undoubtedly, methods for the creation of materials with recognitive abilities similar to those shown in biological molecules such as enzymes and antibodies have been heavily sought after.

Molecular Recognition with Crosslinked Networks. By crosslinking the polymer chains, it is possible to restrict the number of conformations a given chain may adopt. In the formation of a configurationally biomimetic imprinted polymer (CBIP), interactions between a template molecule and the monomer feed molecules leads to the creation of a binding site that is subsequently locked in by polymerization and crosslinking. To date, imprinted structures have been successfully used in chromatographic applications, as sensors, and even as catalytic elements. Simple molecularly imprinted polymers (MIPs) have been made utilizing monomers that had been covalently linked to the functional monomers in order to establish a proper 1:1 stoichiometric ratio. After polymerization, the template molecule was freed through lysis. This covalent technique of imprinting has several advantages including efficient use of all available functional groups and a propensity to form a more uniform binding pocket, but is restrictive in what monomers may be used. A later technique involves imprinting a freely soluble template without the use of covalent linkages. This technique allows for greater flexibility in the choice of functional monomers as well as template molecule. However, reaction conditions need to be more strictly controlled to maximize interaction between template and monomer molecules. In addition, a number of different binding sites may form leading to some nonspecific binding.

The molecular imprinting procedure. The production of a successfully imprinted polymer results in a material with recognitive properties. While many polymerization techniques are amenable to the imprinting procedure, most utilize a free radical technique with either thermal, ultraviolet, or redox methods providing the initiating radicals [49]. Common monomers include the methacrylate and acrylate family of molecules, acrylamides, and other vinyl derivatives as these are readily available, polymerize easily with the free radical technique, and are available with a number of functional groups [50]. In addition to monomer molecules with an array of functional groups, it is crucial to have crosslinking agents that incorporate well into the polymerization and the porosigen. Usually, a crosslinking agent is selected such that it has similar reactivity to the monomers used so as to form a network uniform in crosslinking density [51].

The prepolymerization mixture may include: the functional monomers, crosslinking agent, initiating species, template, porosigen and solvent if desired. As free radical polymerizations are sensitive to the presence of radical scavengers such as dissolved oxygen, the mixture is first purged with an inert gas such as nitrogen. Polymerization is then initiated. Random heteropolymers imprinting is more likely to occur at lower temperatures since entropic effects are lessened, which suggests the use of either a redox or UV initiation method. However, many groups have successfully used thermal initiation, albeit at lower temperatures than normally seen for thermal polymerizations. Following polymerization, the imprinted polymer is swollen in solvent to facilitate the removal of the template molecule. Often times before dialysis, the crosslinked material is crushed and sieved to produce particles of a given diameter in order to facilitate mass transfer. Once free of template, the MIPs are subjected to analysis of their binding ability through a variety of techniques including liquid chromatography, NMR, and microcalorimetry.

Traditionally, the design of biomaterials has focused on biocompatibility—the propensity for a material to not invoke a foreign body response upon implantation or contact in the body. Numerous studies have been done to tailor surface properties so as to not elicit an immune response. The main method has been to functionalize the surface with a hydrophilic molecule, such as grafted poly(ethylene glycol) chains, to mask the foreign surface from protein adsorption. However, it is now being recognized that molecular recognition may play an important role in future biomaterials design. Materials that show good biocompatibility are being further enhanced to include molecular recognition. Potential applications for the present invention include: (1) materials that invoke healing pathways to rebuild tissue in the implantation area; (2) combined sensing element/controlled release device to meter and release appropriate amounts of therapeutic compounds; (3) recognitive materials specific to toxins or deleterious signaling molecules (such as angiotensin) for rapid detoxification in the blood stream; and (4) antibody or enzyme mimics for in vivo use from synthetic materials.

Molecular imprinting can be conducted using one or more biomolecules, e.g., Acetaldehyde (metabolism byproduct); Adenine, adenosine 5V-triphosphate (ATP); Amino acid and peptide derivatives: Z-L-Tyr-OH; Z-L-Phe-OH; Z-DL-Phe-OH; Z-L-Glu-OH; Boc-L-Phe-Gly-Oet; Z-L-Ala-L-Ala-OMe; Z-L-Ala-Gly-L-Phe-OMe; Z-L-Phe-OH; Ampicillin (penicillin antibiotic); a-Amylase (enzyme); Angiotensin II (SA) (competitive inhibitor of; peptide hormone angiotensin II); Bupivacaine (anaesthetic drug); Butein (active anti-EGFR inhibitor); Caffeine (stimulant drug); Cephalexin (antibiotic drug; in a-aminocephalosporins class); Chlorphenamine (anti-histamine drug); Clenbuterol (h adrenergic blocker); Cortisone (steroid); Creatine (metabolite); Creatinine (metabolite); Cholesterol (steroid); Cholic acid sodium salt (bile acid); Carbohydrates: glucose; lactose, maltose, glucose; Glucose; Maltose; lactose; cellobiose; Carbohydrate derivatives: octyl-glucoside, p-nitrophenyl fucoside, p-nitrophenyl galactoside; Peracetylated phenyl a- and h-D-galactosides; Diazepam (i.e., valium, benzodiazepine anxiolytic drug); Enkephalin (neuropeptide); Ephedrine (stimulant drug); Epinephrine (adrenaline hormone); Estradiol (estrogenic steroid hormone); Ethynylestradiol (estrogenic steroid hormone derivative); 9-ethyladenine (nucleotide base derivative); 9-ethyladenine acetate (nucleotide base derivative); Glucose oxidase (enzyme); L-glutamine (amino acid); Histidine (N-terminal) dipeptides; Homocysteine (non-essential amino acid); Horseradish peroxidase (enzyme); Ibuprofen (non-steroidal anti-inflammatory drug); Ketoprofen (non-steroidal anti-inflammatory drug); Lysozyme (enzyme); Morphine (narcotic analgesic drug); Naproxen (non-steroidal anti-inflammatory drug); Nerve agent degradation products; (S)-nilvadipine (dihydropyridine calcium antagonists); Nucleoside base derivatives: tri-O-acetyl adenosine; tri-O-acetyl guanosine; di-O-acetyl thymidine; tri-O-acetyl cytidine; tri-O-acetyl uridine; Nucleotide base derivatives: 9-ethyladenine; 1-propyl thymine; 1-propyl cytosine; 1-cyclohexyl uracil; Oxytocin (hormone); Paracetamol (i.e., acetaminophen, analgesic); Phenylalanine (amino acid); (E)-piceatannol (active anti-EGFR inhibitor); Propanolol (h adrenergic antagonist); Quercetin (active anti-EGFR inhibitor); Ribonuclease A (enzyme); Ricin A and B Chains (toxin bean lectin); (S)-ropivacaine (anaesthetic); Scopolamine (anticholinergic, anti-infective, and analgesic alkaloid drug); Sulfonamides (antibiotic drug); Testosterone (steroid hormone); Tetracycline (antibiotic drug); Theophylline (Bronchodilator drug); Timolol (h adrenergic blocker); Trypsin (enzyme); Tyrosine (amino acid); Tyr-Pro-Leu-Gly-NH2 (tetrapeptide); Leu-enkephalin; Leu-enkephalin; Morphine; Morphine; Ampicillin; S-propranolol; D-phenylalanine; Adenine; 9-ethyladenine; 9-ethyladenine; 9-ethyladenine acetate; Cholesterol; Homocysteine; Trypsin; Theophylline; see, e.g., Hilt & Byne, Configurational biomimesis in drug delivery: molecular imprinting of biologically significant molecule, Advanced Drug Delivery Reviews 56 (2004) 1599-1620, relevant portions and citations incorporated herein by reference.

Protein Imprinting. The potential applications for a recognitive material capable of binding a protein are numerous, including diagnostic devices for protein assays, systems for use in immunochemistry, and separation media for extremely complicated protein mixtures. Production of such materials, however, is difficult for several reasons. First, it is known that the presence of water reduces the interactions between template and monomer since the water molecules compete for hydrogen bonds [33]. Most imprinting, therefore, is done in the presence of non-aqueous media. However, peptides and proteins are especially sensitive to differing solvent conditions and may denature in harsh solvents. Secondly, the large diameter of protein molecules may preclude the use of a densely crosslinked polymeric network since the mesh size of the network is too small to allow for efficient diffusion. It is also unclear how selective a protein imprinted material can be made, and whether subtle changes, such as the process of site directed mutagenesis, can be differentiated by these materials.

In some embodiments, the biomimetic polymer networks may further comprise a moiety. Such compositions may be capable of releasing the moiety in a relatively controlled fashion. The moiety may be present on a target compound, for example, a therapeutic agent. Accordingly, the compositions and methods of the present disclosure may be used in the treatment of a disease. For example, the compositions of the present disclosure may be used as a vehicle to deliver a therapeutic agent to a subject (e.g., a human) in need thereof. The compositions of the present disclosure also may be used to form a medical device or an article. The present disclosure also provides methods of forming a biomimetic polymer network of the present disclosure.

As used herein, the terms "moiety", "recognitive target" and "biomarker" refers to a molecule recognized by a biomimetic polymer network of the present disclosure. The moiety may be covalently bound to a target compound, for example, a therapeutic agent. In this way, the moiety may be used to associate a target compound with a biomimetic polymer network of the present disclosure. The moiety should either already be present on the target compound or capable of being conjugated to a target compound. Conjugation of moieties to therapeutic agents is known in the art, for example, as disclosed in A. Wong and I. Toth, Curr. Med. Chem. 8:1123-36 (2001), the relevant disclosure of which is incorporated by reference. Examples of suitable moieties include, but are not limited, to sugars (e.g., glucose), carbohydrates, peptides, and functional groups. A specific example of a therapeutic agent that comprises a moiety is streptozotocin (R. R. Herr, et al., J. Am. Chem. Soc. 89:4808-09 (1967)), which has a glucose moiety.

In certain embodiments, the moiety is a sugar. For example, the sugar may be a monosaccharide. Monosaccharides have the chemical formula (CH2O)n and the chemical structure H(CHOH)nC=O(CHOH)mH. If n or m is zero, it is an aldose, otherwise it is a ketose. Monosaccharides may include aldoses, trioses (e.g., glyceraldehyde), tetroses (e.g., threose), pentoses (e.g., ribose, xylose), hexoses (e.g. glucose, fructose, mannose, galactose), ketoses, trioses, tetroses, pentoses (e.g., ribulose), hexoses (e.g., fructose). Any of the L and D isomers of a sugar also may be used, although the D isomer may be more preferred for biological applications. Other examples of suitable sugars include polysaccharides. Polysaccharides have a general formula of $C_n(H_2O)_{n-1}$ where n is usually a large number up to 500. Disaccharides, such as, for example, sucrose, lactose, maltose, and the like may be used. Yet another example of suitable sugars includes oligosaccharides and low molecular weight carbohydrates (e.g., having a molecular weight no greater than about 2,000 Da). Further, each carbon atom that supports a —OH group (except for the first and last) is chiral, giving rise to a number of isomeric forms all with the same chemical formula.

Specific embodiments may use the following monosaccharides as moieties: monoses, dioses, trioses, tetroses, pentoses, aldo-pentoses, including arabinose, ribose, deoxyribose and xylose, keto-pentoses including ribulose, hexoses including aldo-hexoses such as: allose, altrose, galactose, glucose, mannose and talose, and keto-hexoses such as fructose, heptoses including keto-heptoses such as mannoheptulose and sedoheptulose, octoses such as octolose, 2-keto-3-deoxy-manno-octonateand and nonoses such as sialic acid.

Specific embodiments may use mucopolysaccharides. Mucopolysaccharides are long unbranched polysaccharides consisting of a repeating disaccharide unit. This unit consists of an N-acetyl-hexosamine and a hexose or hexuronic acid, either or both of which may be sulfated. Members of this family vary in the type of hexosamine, hexose or hexuronic acid unit they contain, e.g., glucuronic acid, iduronic acid, galactose, galactosamine, and glucosamine. They also vary in the geometry of the glycosidic linkage. Specific example polysaccharides that may be used as moieties include: chondroitin sulphate, dermatan sulphate, keratan sulphate, heparan sulphate, heparin, sodium heparin, hyaluronic acid and hyaluronan.

In other embodiments, the moiety may be a lipid or a short amino acid sequence (e.g., a sequence of about twenty amino acids in length). In particular, lectins may be used as a moiety. Lectins are carbohydrate-binding proteins involved in a variety of recognition processes and exhibit considerable structural diversity. A large variability in quaternary association resulting from small alterations in essentially the same tertiary structure is a property exhibited specially by legume lectins. The strategies used by lectins to generate carbohydrate specificity include the extensive use of water bridges, post-translational modification and oligomerization. Other carbohydrate-based structures may be used as moieties may be located at www.chem.qmul.ac.uk/iupac/2carb/ (accessed Apr. 27, 2006), incorporated by reference herein.

In general, the compositions of the present disclosure have enhanced affinities (e.g., impart greater affinity, bound ratios greater than 1) for a chosen moiety, among other things, allowing for increased loading efficiency. Accordingly, the compositions of the present disclosure also may be used to increase the loading of a target compound or control the release rate of a target compound or both. The compositions of the present disclosure also may be used for delivery of a therapeutic agent. For example, the compositions of the present disclosure may be used as an excipient or as a vehicle for a therapeutic agent. Specifically, higher quantities of a therapeutic agent having a moiety can be loaded within the biomimetic polymer networks of the present disclosure, therefore enabling for higher doses to be loaded. The release of a moiety may be tailored to give a desired release profile, for example, for sustained release of a therapeutic agent. Thus, when the moiety is bound to a therapeutic agent, treatment with the therapeutic agent may be optimized.

The compositions of the present disclosure may be formed using configurational biomimetic imprinting. Configuration biomimetic imprinting techniques generally involve forming a prepolymerization complex between the template molecule (e.g., a moiety) and functional monomers or functional oligomers (or polymers) with specific chemical structures designed to interact with the template either by covalent chemistry or noncovalent chemistry (self-assembly) or both. Once the prepolymerization complex is formed, the polymerization reaction occurs in the presence of a crosslinking monomer and an appropriate solvent, which controls the overall polymer morphology and macroporous structure. Once the template is removed, the product is a heteropolymer network with specific recognition elements for the template molecule.

The network structure depends upon the type of monomer chemistry (i.e., anionic, cationic, neutral, amphiphilic), the association strength and number of interactions between the monomers and template molecule, the association interactions between monomers and pendent groups, the solvent type and the amount of solvent in the mixture, the reactivity ratios of the monomers, and the relative amounts of reacted monomer species in the structure. Since noncovalent forces are weaker than covalent bonds, an increased number of interactions are needed for stable binding and recognition. On a per-bond basis, noncovalent bonds are 1-3 orders of magnitude weaker. Therefore, a greater number of noncovalent bonding with matching structural orientation is needed for aqueous recognition.

A wide variety of polymers may be used to form the heteropolymer network. These include polymers produced by reaction of acrylamides and all their substituted structures including: methacrylamide, ethacrylamide, isopropyl acrylamide, etc., acrylic acid, methacrylic acid, ethacrylic acid, all alkyl acrylic acids, any dicarboxylic acid, such as crotonic acid, phthalic and terephthalic acid any tricarboxylic acid with itself another monomer of the above list (forming a copolymer), two other monomers from the above list (forming terpolymers), or three or more monomers from the above list forming higher order coplymers. The above may be in linear, branched or grafted form, the grafted chains being exclusively one polymer or copolymers of the above, ionically bound or complexed by hydrogen bonds.

The above may be crosslinked in the presence of crosslinking agents to form insoluble but swellable gels or networks, having the ability to absorb water, physiological fluids, buffers or salt solutions with final swelling as low as 1 weight % of water and as high as 99.9% water.

The above crosslinking may be achieved with ethylene glycol dimethacrylate, ethylene glycol diacrylate, ethylene glycol trimethacrylate, ethylene glycol diacrylate, ethylene glycol multi methacrylate where "multi" stands for n=4 to 200 units ethylene glycol multi acrylate where "multi" stands for n=4 to 200 units same as above but propylene glycol multi methacrylate where "multi" stands for n=1 to 200 units same as above but alkylene glycol multi methacrylate where "multi" stands for n=1 to 200 units. One may also use higher order acrylates and methacrylates including but not limited to 1,1,1 trimethylolethane trimethacrylate (TrMETrMA, Molecular Weight 324.4); 1,1,1 trimethylolpropane triacrylate (TrMPTrA, Molecular Weight 296.3); 1,1,1 trimethylolpropane trimethacrylate (TrMPTrMA, Molecular Weight 338.4); pentaerythritol triacrylate (PETrA, Molecular Weight 298.3); glycerol propoxy triacrylate (GlyPTrA, Molecular Weight 428.5); pentaerythritol tetraacrylate (PETeA, Molecular Weight 353.2); ethoxylated 1,1,1 trimethylolpropane triacrylate (ETrMPTrA, Molecular Weight 428); glycerol propoxylated triacrylate (GlyPTrA, Molecular Weight 428) and glycerol trimethacrylate (GlyTrMA, Molecular Weight 396.3). One may also use with "star polymers" or "dendrimers" with up to 72 independent chains ending in acrylates or methacrylates.

One non-limiting example of an initiator may be IRGACURE® products of the Ciba Geigy company including IRGACURE 184, IRGACURE® 379, CIBA® IRGACURE® 819, and CIBA® IRGACURE® 250. Any other photoinitiator may also be used. The initiator may also be any peroxide including but not limited to benzoyl peroxide, cumyl peroxide, etc. or Azobis isobutyronitrile.

In some embodiments, the biomimetic polymer network of the present disclosure may be formed using a template molecule (e.g., D-glucose) and functional monomers selected to match corresponding template molecule (e.g., glucose binding protein residues, such as aspartate, glutamate, and asparagines, as well as biological mechanisms of action that involve recognition The template molecule may be added in stoichiometric amounts in regard to the functionality of the template molecule. Since solvent interaction can stabilize or destabilize binding in noncovalent systems, functional monomers may be selected based on optimizing specific noncovalent, self-assembly interactions (hydrogen bonding) with the template molecule within an aprotic solvent (e.g., dimethylsulfoxide). Such techniques are generally applicable to template molecules, in which hydrogen bonding, hydrophobic, or ionic contributions will direct recognition of the moiety. The formation of an exemplary biomimetic polymer network of the present disclosure according to the methods of the present disclosure is described below.

The multilayered mimetic structures may be constructed from a variety of coating processes, including pan coating, air-suspension coating, centrifugal extrusion, vibrational nozzle coating, supercritical fluid (SCF) based processing, fluidization (both conventional Wurster coaters such as the Glatt device) and rotating, or spray-drying.

Systems Prepared with Porosigens. The development of highly porous recognitive, low swelling hydrogels can be accomplished using various methods, including gas blowing, induced phase separation, and via the addition of porosigens. These studies employ various porosigens including, e.g., sodium chloride, calcium chloride, and ammonium carbamate.

Sodium Chloride. The first example involved the addition of sodium chloride (NaCl, S271-3, Certified ACS, Fisher Scientific, Fair Lawn, N.J.) to our monomer solution in various concentrations. The composition was then polymerized using the standard protocol and extracted in Milli-Q DI-$H_2O$ for 1-2 days. The films were then removed and placed in a ventilated container inside a drying oven (with desiccant) for 24 hours, after which the films were removed and observed.

TABLE 1

Summary Table for Examples.

| Reference | Recipe | NaCl conc.* |
|---|---|---|
| A | 6.5.1 | 87.85 mol % |
| B | 6.11.1.C | 83.99 mol % |
| C | 6.11.1.B | 75.37 mol % |
| D | 6.7.1 | 68.84 mol % |
| E | 6.11.1.A | 57.60 mol % |
| F | 7.6.1 | 39.24 mol % |

*Measured here in percent (by moles) of the monomer solution.

Ammonium Carbamate. In the second example, ammonium carbamate ($NH_4CO_2NH_2$, Stock 18134, Lot K14Q038, Alfa Aesar, Ward Hill, Mass.) was used as received. It was added to the monomer solution at a concentration of 54.8 mol %.

Calcium Chloride. The third example used calcium chloride ($CaCl_2$, 239224, Batch #06602Co., Aldrich Co., Milwaukee, Wis.) in the monomer solution at a concentration of 48.7 mol %.

Sodium Chloride. Polymerization mixture A was polymerized in the presence of NaCl but produced an unsatisfactory solid film; instead, much of it was left as a liquid in the unpolymerized form and appeared slightly hazy, indicating some polymerization but no crosslinking, perhaps as a result of the high amounts of porosigen present. Mixtures B-F produced be solid films, although some of them were very soft and flaky (uncharacteristic of the type of swellable hydrogels that would be produced sans porosigen).

FIG. 1. A dried film made from Recipe B (84 mol % NaCl) (light microscope, 1620× magnification, 5× objective).

Figure 2:
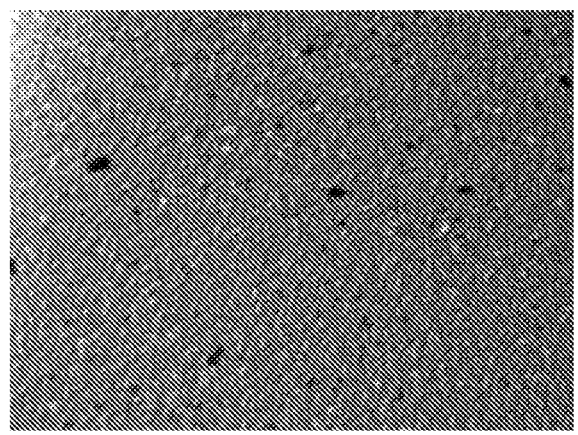
FIG. 2 A dried film made from Recipe E (~58 mol % NaCl) (light microscope, 1620× magnification, 5× objective)

FIG. 2 A dried film made from Recipe E (58 mol % NaCl) (light microscope, 1620× magnification, 5× objective).

FIGS. 1 and 2 above indicate an observable difference in surface morphology as a result of a 26 mol % decrease in the concentration of porosigen present in the mixture. When exposed to a glucose-water mixture (at a concentration of 100 mg/dL) all of the films B-F demonstrated a substantial tendency to absorb water (more than non-porous samples), while they showed characteristic signs of self-rupturing with disintegration as apparent in FIG. 3 below.

Figure 3:
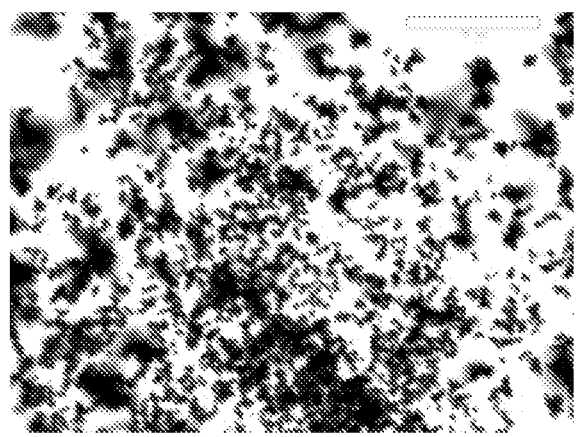
FIG. 3. Presence of disintegrated portions of recipe E films 24 hours after exposure to 200 mg/dL glucose-water (light microscope, 1620× magnification, 50× objective)

FIG. 3. Presence of disintegrated portions of recipe E films 24 hours after exposure to 200 mg/dL glucose-water (light microscope, 1620× magnification, 50× objective)

Further investigation will be done on the effects of various procedural variables on the recognitive properties of the films, including methods of polymerization, constitution of the solvent mixture, and the methods of washing and drying.

Ammonium Carbamate and Calcium Chloride. The configurationally biomimetic imprinted polymers (CBIP) produced in the presence of ammonium carbamate and calcium chloride porosigens demonstrated little difference in effective recognition from the polymers made of sodium chloride porosigen. The use of ammonium carbamate (55 mol %) produced less rigid films than comparable films made of sodium chloride; they appeared opaque and flaky. Films made of calcium chloride were less flaky but were still opaque and "fragile".

Figure 4:
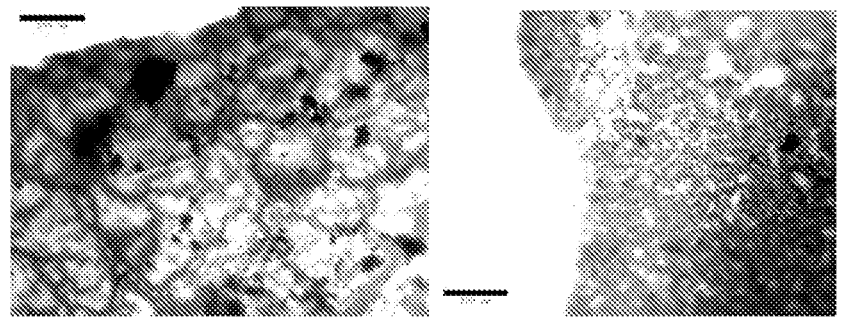
FIG. 4. Photos taken under a light microscope (1620× magnification, 50× objective) of films made of ammonium carbamate (left) and of calcium chloride (right) porosigens.

FIG. 4. Photos taken under a light microscope (1620× magnification, 50× objective) of films made of ammonium carbamate (left) and of calcium chloride (right) porosigens.

The results of this study demonstrate that for the purposes of molecular recognition, the use of sodium chloride is preferable to the use of either of these two porosigens.

Figure 5:
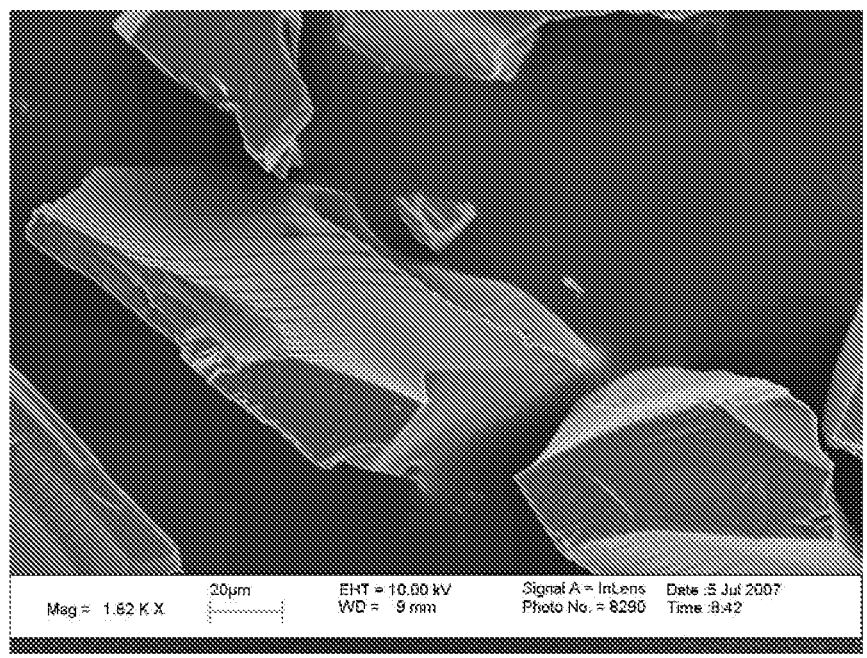
FIG. 5. An SEM photograph of CBIP particles polymerized without the presence and crushed by mortar and pestle into microparticles.

Electron Microscopy. In order to more easily characterize the surface properties of polymer films made in the presence of porosigens, scanning electron microscopy was used to take images of the surface of each of the films. FIG. 5. An SEM photograph of CBIP particles polymerized without the presence and crushed by mortar and pestle into microparticles.

Figure 6:
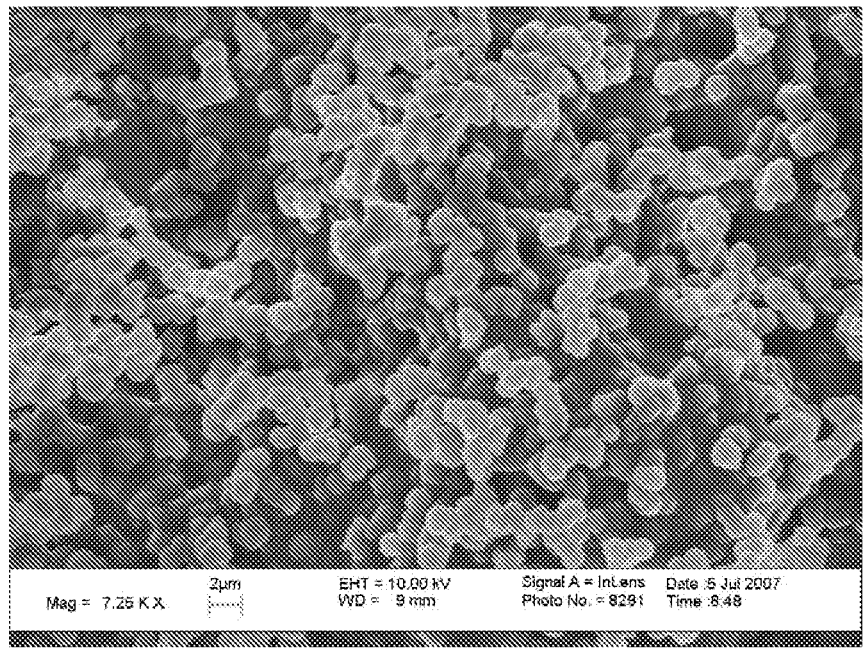
FIG. 6. An SEM of CBIP films prepared with sodium chloride as a porosigen (recipe B).

FIG. 5 shows the shape and size of a typical microparticle made from CBIP films prepared in the absence of porosigens. FIG. 6 shows the porous CBIP material prepared via recipe B in the presence of sodium chloride. This is a unique morphology that is the result of two phenomena: (i) presence of dissolving NaCl that creates large pores; and (ii) a "salting out process in the presence of NaCl that makes the recognitive polymer form spherical microparticles agglomeration during film production. FIG. 6. An SEM of CBIP films prepared with sodium chloride as a porosigen (recipe B).

Figure 7:
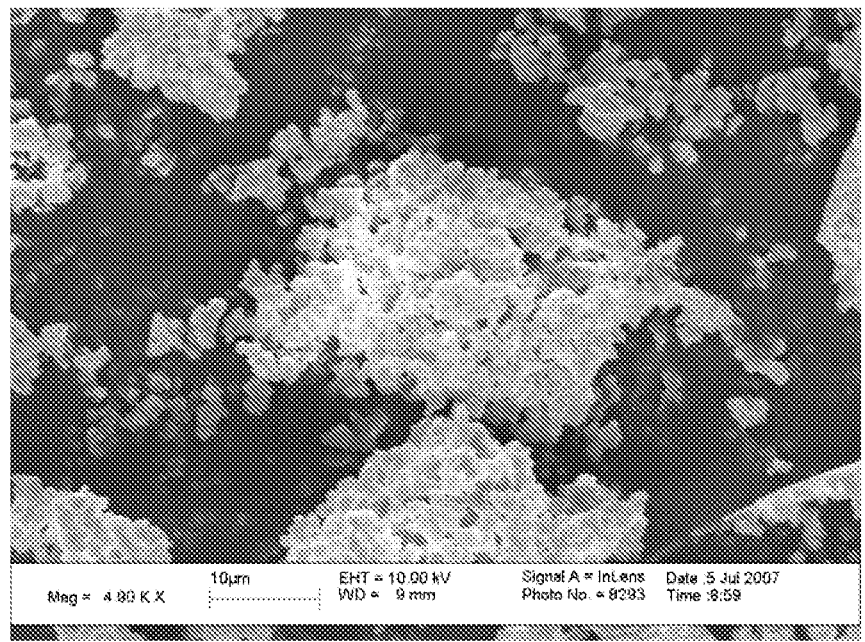
FIG. 7. An SEM of CBIP films prepared with ammonium carbamate as a porosigen (55 mol %).

FIG. 7. An SEM of CBIP films prepared with ammonium carbamate as a porosigen (55 mol %).

Figure 8:
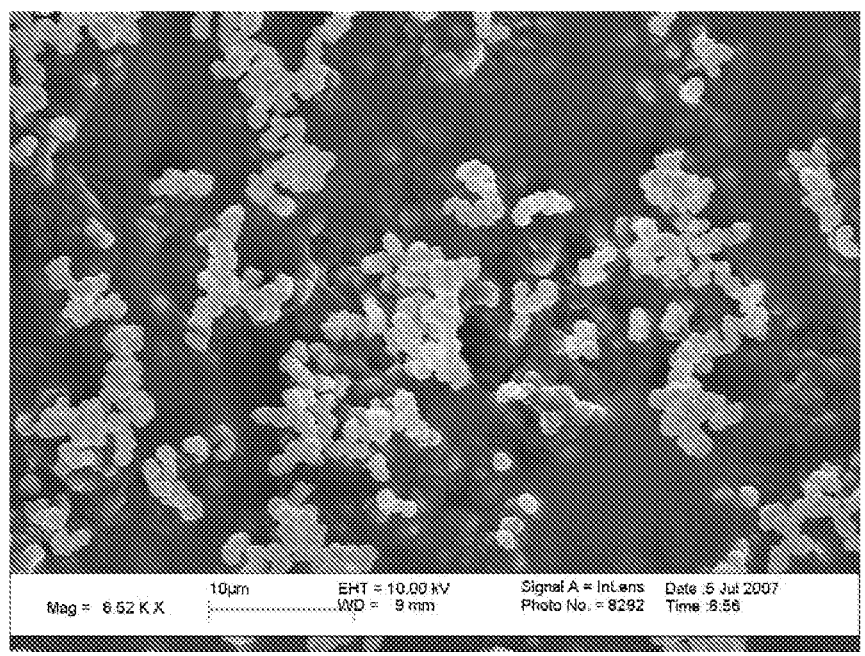
FIG. 8. An SEM of films made from calcium chloride porosigen (49 mol %).

FIG. 8. An SEM of films made from calcium chloride porosigen (49 mol %).

The same morphology is observed with the other two porosigens as shown in FIGS. 7 and 8; they are aggregated globules of polymerized material made from porosigen-mixtures.

One example of a mixture for creating an epinephrine MIP film involves the same monomer mixture (MAA with EGDMA crosslinker), while the solvent would be a mixture of acetonitrile and benzyl alcohol (3:2 v/v A batch of epinephrine-imprinted polymers was prepared using a protocol analogous to the one used for glucose MIP films with similar results. The films were consistent, clear, and solid.

The following are the Examples of the mixtures described herein above, made with porosigen.

Sodium Chloride Recipes

Example A

| 6.5.1 | Amount | Moles | % Wt. | % Mol. | Reactants | |
|---|---|---|---|---|---|---|
| D-Glucose | 0.0945 g | 0.0005245 mol | 0.783% | 0.184% | 0.495 | mol % |
| MAA | 0.2224 g | 0.0025842 mol | 1.842% | 0.907% | 2.440 | mol % |
| DI-H$_2$O | 2.4050 g | 0.1334628 mol | 19.92% | 46.83% | — | |
| EtOH | 2.1003 g | 0.0455893 mol | 17.40% | 16.00% | — | |
| DMPA | 0.0484 g | 0.0001888 mol | 0.401% | 0.066% | 0.178 | mol % |
| EGDMA | 1.7620 g | 0.0095761 mol | 14.60% | 3.360% | 9.041 | mol % |
| NaCl | 5.4380 g | 0.0930495 mol | 45.05% | 32.65% | 87.85 | mol % |
| TOTAL | 12.071 g | 0.2849752 mol | | | 0.1059231 | mol |

Example B

| 6.11.1.C | Amount | Moles | % Wt. | % Mol. | Reactants | |
|---|---|---|---|---|---|---|
| D-glucose | 0.0918 g | 0.0005095 mol | 0.6922% | 0.1680% | 0.6286 | mol % |
| MAA | 0.2136 g | 0.0024820 mol | 1.6105% | 0.8182% | 3.0621 | mol % |
| DI-H$_2$O | 2.0000 g | 0.1109878 mol | 15.080% | 36.586% | | |
| Ethanol | 5.1285 g | 0.1113197 mol | 38.668% | 36.695% | | |
| EGDMA | 1.8000 g | 0.0097826 mol | 13.572% | 3.2247% | 12.069 | mol % |
| DMPA | 0.0500 g | 0.0001951 mol | 0.3770% | 0.0643% | 0.2407 | mol % |
| NaCl | 3.9790 g | 0.0680850 mol | 30.001% | 22.444% | 83.999 | mol % |
| Total | 13.263 g | 0.3033617 mol | | | 0.0810542 | mol |

Example C

| 6.11.1.B | Amount | Moles | % Wt. | % Mol. | Reactants | |
|---|---|---|---|---|---|---|
| D-glucose | 0.0918 g | 0.0005095 mol | 0.7912% | 0.0927% | 0.9677 | mol % |
| MAA | 0.2136 g | 0.0024820 mol | 1.8409% | 0.4513% | 4.7140 | mol % |
| DI-H$_2$O | 2.0000 g | 0.1109878 mol | 17.367% | 20.183% | — | |
| Ethanol | 5.1285 g | 0.1113197 mol | 44.200% | 20.243% | — | |
| EGDMA | 1.8000 g | 0.0097826 mol | 15.513% | 1.7789% | 18.580 | mol % |
| DMPA | 0.0500 g | 0.0001951 mol | 0.4309% | 0.0355% | 0.3706 | mol % |
| NaCl | 2.3191 g | 0.0396821 mol | 19.987% | 7.2160% | 75.368 | mol % |
| Total | 11.603 g | 0.2749588 mol | | | 0.0526513 | mol |

Example D

| 6.7.1 | Amount | Moles | % Wt. | % Mol. | Reactants | |
|---|---|---|---|---|---|---|
| D-Glucose | 0.0915 g | 0.0005079 mol | 1.098% | 0.230% | 1.217 | mol % |
| MAA | 0.2165 g | 0.0025157 mol | 2.597% | 1.141% | 6.030 | mol % |
| DI-H$_2$O | 2.4000 g | 0.1331853 mol | 28.79% | 60.40% | — | |
| EtOH | 2.1000 g | 0.0455828 mol | 25.19% | 20.67% | — | |
| DMPA | 0.0496 g | 0.0001935 mol | 0.595% | 0.088% | 0.464 | mol % |
| EGDMA | 1.8003 g | 0.0097842 mol | 21.60% | 4.438% | 23.45 | mol % |
| NaCl | 1.6785 g | 0.0287208 mol | 20.13% | 13.03% | 68.84 | mol % |
| TOTAL | 8.3364 g | 0.2204902 mol | | | 0.0417221 | mol |

Example E

| 6.11.1.A | Amount | Moles | % Wt. | % Mol. | Reactants |
|---|---|---|---|---|---|
| D-glucose | 0.0918 g | 0.0005095 mol | 0.8901% | 0.2015% | 1.6657 mol % |
| MAA | 0.2136 g | 0.0024820 mol | 2.0710% | 0.9814% | 8.1142 mol % |
| DI-H₂O | 2.0000 g | 0.1109878 mol | 19.391% | 43.887% | — |
| Ethanol | 5.1285 g | 0.1113197 mol | 49.724% | 44.018% | — |
| EGDMA | 1.8000 g | 0.0097826 mol | 17.452% | 3.8682% | 31.922 mol % |
| DMPA | 0.0500 g | 0.0001951 mol | 0.4848% | 0.0771% | 0.6378 mol % |
| NaCl | 1.0297 g | 0.0176191 mol | 9.9835% | 6.9669% | 57.601 mol % |
| Total | 10.314 g | 0.2528958 mol | | | 0.0305883 mol |

Example F

| 7.6.1 | Amount | Moles | % Wt. | % Mol. | Reactants |
|---|---|---|---|---|---|
| D-glucose | 0.0918 g | 0.0005095 mol | 0.9393% | 0.2091% | 2.387 mol % |
| MAA | 0.2136 g | 0.0024820 mol | 2.1855% | 1.0187% | 11.63 mol % |
| DI-H₂O | 2.0000 g | 0.1109878 mol | 20.464% | 45.552% | — |
| Ethanol | 5.1285 g | 0.1113197 mol | 52.474% | 45.688% | — |
| EGDMA | 1.8000 g | 0.0097826 mol | 18.417% | 4.0150% | 45.83 mol % |
| DMPA | 0.0500 g | 0.0001951 mol | 0.5116% | 0.0801% | 0.914 mol % |
| NaCl | 0.4895 g | 0.0083758 mol | 5.0085% | 3.4376% | 39.24 mol % |
| Total | 9.7734 g | 0.2436525 mol | | | 0.021345 mol |

Recipes for Polymers Seen Under SEM

Ammonium Carbamate

Example G

| 6.25.1 | Amount | Moles | Percent (Wt.) | Percent (Mol.) | Monomers | Reactants | Solvent |
|---|---|---|---|---|---|---|---|
| D-glucose | 0.10023 g | 0.0005563 mol | 0.954% | 0.222% | — | 2.973 wt % | — |
| MAA | 0.19630 g | 0.0022810 mol | 1.869% | 0.910% | 18.55 mol % | 5.823 wt % | — |
| DI-Water | 2.00000 g | 0.1109878 mol | 19.05% | 44.26% | — | — | 28.05 wt % |
| Ethanol | 5.13000 g | 0.1113523 mol | 48.85% | 44.40% | — | — | 71.95 wt % |
| DMPA | 0.05020 g | 0.0001959 mol | 0.478% | 0.078% | 1.593 mol % | 1.489 wt % | — |
| EGDMA | 1.80730 g | 0.0098222 mol | 17.21% | 3.917% | 79.86 mol % | 53.61 wt % | — |
| AmCarb | 1.21720 g | 0.0155911 mol | 11.59% | 6.217% | — | 36.11 wt % | — |
| Total | 10.5012 g | 0.2507866 mol | | | 0.012299 mol | 3.37123 g | 7.13 g |

Reactants: 32.1 wt %, Solvent: 67.9 wt %

Calcium Chloride

Example H

| 6.25.2 | Amount | Moles | Percent (Wt.) | Percent (Mol.) | Monomers | Reactants | Solvent |
|---|---|---|---|---|---|---|---|
| D-glucose | 0.10320 g | 0.0005728 mol | 0.981% | 0.231% | — | 3.047 wt % | — |
| MAA | 0.20230 g | 0.0023507 mol | 1.924% | 0.950% | 19.03 mol % | 5.973 wt % | — |
| DI-Water | 2.0000 g | 0.1109878 mol | 19.02% | 44.84% | — | — | 28.05 wt % |
| Ethanol | 5.13000 g | 0.1113523 mol | 48.78% | 44.99% | — | — | 71.95 wt % |
| DMPA | 0.05510 g | 0.0002150 mol | 0.524% | 0.087% | 1.741 mol % | 1.627 wt % | — |
| EGDMA | 1.80060 g | 0.0097859 mol | 17.12% | 3.954% | 79.23 mol % | 53.17 wt % | — |
| CalChl | 1.22560 g | 0.0122453 mol | 11.65% | 4.947% | — | 36.19 wt % | — |
| Total | 10.5168 g | 0.2475100 mol | | | 0.012299 mol | 3.3868 g | 7.13 g |

Reactants: 32.2 wt %, Solvent: 67.8 wt %

Sodium Chloride

Example I

| 6.11.1.C | Amount | Moles | Percent (Wt.) | Percent (Mol.) | Monomers | Reactants | Solvent |
|---|---|---|---|---|---|---|---|
| D-glucose | 0.0918 g | 0.0005095 mol | 0.6922% | 0.1680% | — | 1.496 wt % | — |
| MAA | 0.2136 g | 0.0024820 mol | 1.6105% | 0.8182% | 19.92 mol % | 3.482 wt % | — |
| DI-H$_2$O | 2.0000 g | 0.1109878 mol | 15.080% | 36.586% | — | — | 28.06 wt % |
| Ethanol | 5.1285 g | 0.1113197 mol | 38.668% | 36.695% | — | — | 71.94 wt % |
| EGDMA | 1.8000 g | 0.0097826 mol | 13.572% | 3.2247% | 78.51 mol % | 29.34 wt % | — |
| DMPA | 0.0500 g | 0.0001951 mol | 0.3770% | 0.0643% | 1.566 mol % | 0.815 wt % | — |
| NaCl | 3.9790 g | 0.0680850 mol | 30.001% | 22.444% | — | 64.86 wt % | — |
| Total | 13.263 g | 0.3033617 mol | | | 0.012460 mol | 6.1344 g | 7.1285 g |

Reactants: 46.3 wt %, Solvent: 53.7 wt %

No Porosigen

Example J

| BLE53 | Amount | Moles | Percent (Wt.) | Percent (Mol.) | Monomers | Reactants | Solvent |
|---|---|---|---|---|---|---|---|
| D-glucose | 0.1820 g | 0.0010102 mol | 1.441% | 0.290% | — | 4.665 wt % | — |
| MAA | 0.4182 g | 0.0048594 mol | 3.312% | 1.396% | 21.36 mol % | 10.72 wt % | — |
| DI-H$_2$O | 3.9920 g | 0.2215316 mol | 31.61% | 63.65% | — | — | 45.75 wt % |
| Ethanol | 4.7340 g | 0.1027570 mol | 37.49% | 29.52% | — | — | 54.25 wt % |
| EGDMA | 3.2700 g | 0.0177717 mol | 25.90% | 5.106% | 72.11 mol % | 83.82 wt % | — |
| DMPA | 0.0311 g | 0.0001213 mol | 0.246% | 0.035% | 0.533 mol % | 0.797 wt % | — |
| Total | 12.6273 g | 0.3480512 mol | | | 0.022752 mol | 3.9013 g | 8.726 g |

Reactants: 30.9 wt %, Solvent: 69.1 wt %

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention.

All such similar substitutes and modifications apparent to those skilled in the art are deemed to be within the spirit, scope and concept of the invention as defined by the appended claims.

REFERENCES

E. Jabbari et al. European Application EP20040782412 Publication date Jun. 7, 2006 hydrogel porogens for fabricating biodegradable scaffolds.

A Domschke and V. M. Francis, Porous hydrogels, U.S. Pat. No. 6,897,271, Issued on May 24, 2005.

Hossein Omidian, Jose G. Rocca and Kinam Park, Advances in superporous hydrogels, J Controlled release, 102, 3-12 (2005).

Kabiri K.; Omidian H.; Zohuriaan-Mehr M. Novel approach to highly porous superabsorbent hydrogels, Polymer International, 52, 2003, pp. 1158-116.

Badiger, M V: McNeill, M E: Graham, N B, Porogens in the preparation of microporous hydrogels based on poly(ethylene oxides), Biomaterials. 1993; 14: 1059-63.

What is claimed is:

1. A composition comprising:
   one or more active agents disposed in a recognitive polymeric matrix comprising
      a methacrylic acid polymerized to form a polymeric hydrogel matrix;
      a porosigen distributed in the polymeric hydrogel matrix wherein the porosigen comprises sodium chloride in a final weight percent of between 20 and 90 percent of the composition;
      a recognitive molecule disposed in the polymeric hydrogel matrix and associated with the one or more active agents to form a porous recognitive polymeric hydrogel,
   wherein the recognitive molecule recognizes a recognized agent and the porous recognitive polymeric hydrogel dissociates in the presence of the recognized agent to release the one or more active agents, wherein the recognitive agent comprises D-glucose and the one or more active agents comprising insulin.

2. The composition of claim 1, wherein the porous recognitive polymeric hydrogel is swellable and swells, cracks, dissolves, dissociates or melts under conditions of low water or humidity.

3. The composition of claim 1, wherein the porosigen has a mole percent of between 30 and 90 mole percent of the composition during the polymerization of the polymer.

4. The composition of claim 1, wherein a loss of structural integrity of the porous recognitive polymeric hydrogel is due to:
   osmosis upon the presence and binding of the molecule leading to rupture due to swelling;
   change of the solubility of the polymeric network leading to polymer dissolution;
   local temperature changes leading to expansion melting or both of the polymeric network or combinations thereof.

5. The composition of claim 1, wherein the recognitive polymeric matrix is formed into one or more layers.

6. The composition of claim 1, wherein the recognitive polymeric matrix is formed into one or more layers, each of which recognizes a different recognized agent and each of which provides a barrier to the release of one or more different active or inert agents or both.

7. The composition of claim 1, wherein the recognitive polymeric matrix is formed into a sphere, film, planar, semi-spherical, cylinder, rod, hemispheres, conical, hemi-cylinders or combinations thereof.

* * * * *